United States Patent
Smith et al.

(10) Patent No.: US 6,784,797 B2
(45) Date of Patent: Aug. 31, 2004

(54) MICROPROCESSOR BASED BED PATIENT MONITOR

(75) Inventors: Toby E. Smith, Broken Arrow, OK (US); Craig L. Cooper, Inola, OK (US); Fred H. Holmes, Cleveland, OK (US); Patrick W. Lovely, Tulsa, OK (US)

(73) Assignee: Bed-Check Corporation, Tulsa, OK (US)

(*) Notice: Subject to any disclaimer, the term of this patent is extended or adjusted under 35 U.S.C. 154(b) by 0 days.

(21) Appl. No.: 10/210,817

(22) Filed: Aug. 1, 2002

(65) Prior Publication Data

US 2003/0063010 A1 Apr. 3, 2003

Related U.S. Application Data

(63) Continuation-in-part of application No. 09/257,750, filed on Feb. 25, 1999, now Pat. No. 6,441,742, which is a continuation-in-part of application No. 09/031,363, filed on Feb. 26, 1998, now Pat. No. 6,111,509.

(51) Int. Cl.$^7$ .............................................. G08B 23/00
(52) U.S. Cl. ............................... 340/573.4; 340/573.1; 340/286.07
(58) Field of Search ..................... 340/310.01, 310.06, 340/310.07, 539.1, 539.11, 539.12, 539.14, 539.15, 539.19, 286.06, 286.07, 573.1, 573.4, 286.11; 600/483, 529

(56) References Cited

U.S. PATENT DOCUMENTS

| | | |
|---|---|---|
| 4,179,692 A | 12/1979 | Vance |
| 4,295,133 A | 10/1981 | Vance |
| 4,484,043 A | 11/1984 | Musick et al. |
| 4,565,910 A | 1/1986 | Musick et al. |
| 4,700,180 A | 10/1987 | Vance |
| 4,792,990 A | * 12/1988 | Beyers, Jr. ............... 455/234.2 |
| 4,803,625 A | * 2/1989 | Fu et al. ..................... 600/483 |

(List continued on next page.)

FOREIGN PATENT DOCUMENTS

| | | |
|---|---|---|
| EP | 0 191 906 | 8/1996 |
| WO | WO 95 03596 | 2/1995 |
| WO | WO 95 22363 | 8/1995 |
| WO | WO 96 03727 | 2/1996 |
| WO | WO 97 06519 | 2/1997 |
| WO | WO 98 10391 | 3/1998 |

OTHER PUBLICATIONS

Patent Abstracts of Japan. vol. 097, No. 004, Apr. 30, 1997 and JP 08 322810 A (Nippon Denshi Kogyo KK), Dec. 10, 1996.
Patent Abstracts of Japan, vol. 095, No. 010, Nov. 30, 1995 & JP 07 168990 A (Canon Inc.), Jul. 4, 1995.

*Primary Examiner*—Van T. Trieu
(74) *Attorney, Agent, or Firm*—Fellers, Snider, Blankenship, Bailey & Tippens, P.C.

(57) ABSTRACT

This invention relates generally to monitoring systems and more particularly concerns devices and systems used to monitor patients the presence and absence of a patient from a bed, chair, etc. The preferred environment in which the instant invention would be used would be a hospital or other care giving facility, wherein patients who are at risk of falling might left unattended while they are seated or lying. According to a first aspect of the instant invention, a microprocessor-based patient monitor is disclosed which includes a loudspeaker that emits alarms synthesized by the microprocessor. The microprocessor synthesizes any one of multiple alarm sounds under software control and activates and deactivates the alarm in response to the electronic signals received from an attached sensor and a user interface.

26 Claims, 22 Drawing Sheets

U.S. PATENT DOCUMENTS

| | | |
|---|---|---|
| 5,224,496 A | 7/1993 | Palmer et al. |
| D361,462 S | 8/1995 | Newham |
| 5,519,380 A * | 5/1996 | Edwards ................. 340/573.1 |
| 5,554,835 A | 9/1996 | Newham |
| 5,561,412 A | 10/1996 | Novak et al. |
| 5,600,108 A | 2/1997 | Newham |
| 5,623,760 A | 4/1997 | Newham |
| 5,633,627 A | 5/1997 | Newham |
| 5,640,145 A | 6/1997 | Newham |
| 5,654,694 A | 8/1997 | Newham |
| 5,699,038 A | 12/1997 | Ulrich et al. |
| 5,704,366 A * | 1/1998 | Tacklind et al. ............. 600/529 |
| 5,838,223 A * | 11/1998 | Gallant et al. ......... 340/286.07 |
| 5,945,914 A | 8/1999 | Holmes et al. |
| 6,111,509 A | 8/2000 | Holmes |
| 6,292,102 B1 | 9/2001 | Smith |
| 6,297,738 B1 * | 10/2001 | Newham ................. 340/573.1 |
| 6,307,476 B1 | 10/2001 | Smith et al. |
| 6,417,777 B2 | 7/2002 | Fitzgerald et al. |
| 6,441,742 B1 | 8/2002 | Lovely et al. |

* cited by examiner

MICROPROCESSOR BASED BED PATIENT MONITOR

RELATED APPLICATIONS

This application is a continuation-in-part of application Ser. No. 09/257,750, filed on Feb. 25, 1999, now U.S. Pat. No. 6,441,742, which is in turn a continuation-in-part of application Ser. No. 09/031,363, filed on Feb. 26, 1998, now U.S. Pat. No. 6,111,509, the disclosures of which are incorporated herein by reference.

BACKGROUND OF THE INVENTION

This invention relates generally to monitoring systems and more particularly concerns devices and systems used to monitor bed patients in hospital or other care giving environments.

It is well documented that the elderly and post-surgical patients are at a heightened risk of falling. There are many reasons for this but, broadly speaking, these individuals are often afflicted by gait and balance disorders, weakness, dizziness, confusion, visual impairment, and postural hypotension (i.e., a sudden drop in blood pressure that causes dizziness and fainting), all of which are recognized as potential contributors to a fall. Additionally, cognitive and functional impairment, and sedating and psychoactive medications are also well recognized risk factors.

A fall places the patient at risk of various injuries including sprains, fractures, and broken bones—injuries which in some cases can be severe enough to eventually lead to a fatality. Of course, those most susceptible to falls are often those in the poorest general health and least likely to recover quickly from their injuries. In addition to the obvious physiological consequences of fall-related injuries, there are also a variety of adverse economic and legal consequences that include the actual cost of treating the victim and, in some cases, caretaker liability issues.

In the past, it has been commonplace to treat patients that are prone to falling by limiting their mobility through the use of restraints, the underlying theory being that if the patient is not free to move about, he or she will not be as likely to fall. However, research has shown that restraint-based patient treatment strategies are often more harmful than beneficial and should generally be avoided—the emphasis today being on the promotion of mobility rather than immobility. Among the more successful mobility-based strategies for fall prevention include interventions to improve patient strength and functional status, reduction of environmental hazards, and staff identification and monitoring of high-risk hospital patients and nursing home residents.

Of course, monitoring high-risk patients, as effective as that care strategy might appear to be in theory, suffers from the obvious practical disadvantage of requiring additional staff if the monitoring is to be in the form of direct observation. Thus, the trend in patient monitoring has been toward the use of electrical devices to signal changes in a patient's circumstance to a caregiver who might be located either nearby or remotely at a central monitoring facility, such as a nurse's station. The obvious advantage of an electronic monitoring arrangement is that it frees the caregiver to pursue other tasks away from the patient. Additionally, when the monitoring is done at a central facility a single nurse can monitor multiple patients which can result in decreased staffing requirements.

Generally speaking, electronic monitors work by first sensing an initial status of a patient, and then generating a signal when that status changes, e.g., he or she has sat up in bed, left the bed, risen from a chair, etc., any of which situations could pose a potential cause for concern in the case of an at-risk patient. Electronic bed and chair monitors typically use a pressure sensitive switch in combination with a separate monitor /microprocessor. In a common arrangement, a patient's weight resting on a pressure sensitive mat (i.e., a "sensing" mat) completes an electrical circuit, thereby signaling the presence of the patient to the microprocessor. When the weight is removed from the pressure sensitive switch, the electrical circuit is interrupted, which fact is sensed by the microprocessor. The software logic that drives the monitor is typically programmed to respond to the now-opened circuit by triggering some sort of alarm—either electronically (e.g., to the nursing station via a conventional nurse call system) or audibly (via a built-in siren). Some examples of devices that operate in this general fashion may be found in U.S. Pat. Nos. 4,484,043, 4,565,910, 5,554,835, and 5,634,760, the disclosures of which are incorporated herein by reference.

That being said, patient monitoring systems that rely on sensor mats to detect the presence of a patient in a bed suffer from a variety of drawbacks. For example, the bed monitoring systems currently available in the marketplace feature externally accessible configuration switches that allow the caregiver to reconfigure the device at will and to adjust parameters such as the duration of the alarm, and the time lapse between the sensing of the "empty bed" condition and the sounding of an alarm. External switching makes tampering with the system extremely easy and makes it more difficult to establish and maintain a hospital-wide policy with respect to monitor settings.

A further problem with conventional bed monitoring systems is that they use oscillating transducers in their alarm audio circuits, resulting in single frequency audio alarms. Since bed monitor alarms are frequently employed in environments in which a multiplicity of other problems might also trigger audio alarms, if the single alarm sound provided by the bed monitor happens to be similar to one or more other alarm sounds heard in response to different monitors, confusion and consequential lengthened response times to patient monitor alarms may result.

Those skilled in the art know that there are many nurse call station configurations and it is to the economic advantage of a manufacturer to be able to accommodate all of them. However, another problem with the present state-of-the-art in bed monitoring systems is that they are typically pre-configured internally at the factory for one particular type of nurse call station. Thus, if the unit is misconfigured when it arrives at an installation, it may be necessary to summon a medical technician to reconfigure it, since internal modifications to the unit are required to adapt it to different call station types. This can result in additional expense and delay in getting the unit correctly configured and into operation. Further, there are many hospitals that use multiple incompatible nurse call system types, each having been separately added as a new building or wing was constructed. The inability to quickly and reliably move electronic monitors between these systems means that the hospital will generally be required to maintain excess inventory of each type of compatible monitor, a result that ultimately adds to the health care costs borne by the consumer/patient.

Still another failure in known bed monitoring systems is that they do not provide a method of accumulating statistical data relating to the operation of the unit including, for example, the response times of the caregiver to alarm conditions. This sort of information could be very helpful to the maintenance and proper operation of the monitor, and for caregiver quality control purposes.

It is, therefore, a primary object of this invention to provide a patient monitor that is microprocessor-based so as to be reconfigurable by the uploading of configuration data to an electronically erasable programmable read only memory accessible by the microprocessor. A further object of this invention is to provide a microprocessor based patient monitor which synthesizes multiple alarm sounds in software for selection by the caregiver. It is also an object of this invention to provide a microprocessor based patient monitor having a nurse call interface allowing interconnection with any nurse call station without modification of the monitor. Yet another object of this invention is to provide a microprocessor based patient monitor having an electrically erasable programmable read only memory accessible by the microprocessor for logging statistical data with respect to the use of the monitor and the response time of the caregiver who is responding to the alarm. Another object of this invention is to provide a microprocessor based bed patient monitor which permits the downloading of the logged statistical data to a host microprocessor connected to the system. It is still another object of the instant invention to provide a system for configuration of monitor parameters and for recalling and analyzing statistical data accumulated therein.

Heretofore, as is well known in the bed monitor arts, there has been a need for an invention to address and solve the above-described problems. Accordingly, it should now be recognized, as was recognized by the present inventor, that there exists, and has existed for some time, a very real need for a electronic patient monitor that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with the invention, a patient monitor is provided in which a processor receiving electronic signals from a sensor indicating the presence on the sensor and absence from the sensor of a patient is combined with an alarm system which includes a loudspeaker driven by a power amplifier which responds to an input signal derived from a programmable volume control to produce an aural alarm. The processor synthesizes at least one and preferably multiple alarm sounds under software control, operates the programmable volume control of the alarm system to select the decibel level of the alarm and activates and deactivates the alarm in response to the electronic signals received from the sensor and a user interface. An electrically erasable programmable read-only memory (or similar nonvolatile memory) accessible by the processor stores a plurality of alarm sounds for selection by the processor for synthesis of the selected alarm sound. In addition, the electrically erasable programmable read-only memory stores multiple decibel levels for selection by the processor of the desired decibel level of the alarm sound. In the preferred embodiment, the patient monitor will be used to sense the presence of patient who is lying in a bed, however, it should be noted and remembered this monitor could also be used in other sorts of applications, including with chair and toilet monitors.

Preferably, the electrically erasable programmable read-only memory also permits storage of a plurality of options for the delay time between initiation of the absence of a patient from the sensor and the activation of the alarm by the processor. Furthermore, the monitor is preferably provided with an external switch connected to the processor for caregiver selection of the delay time from the plurality of delay time options.

It is also preferred that the electrically erasable programmable read-only memory log usage data with respect to the monitor including the total hours of use of the monitor, the total time of alarms sounded by the monitor, the total number of alarms sounded by the monitor and the response time between the most recent sounding of an alarm and a subsequent operation of the monitor by the responding caregiver. The monitor will include a port for downloading the log usage data to a host computer.

The monitor also includes a nurse call interface having a relay which is energized when the power amplifier is de-energized and which has a normally opened contact, a normally closed contact and a common contact for interconnecting the monitor to a nurse call system to one of the normally opened and normally closed contacts so that the monitor requires no modification to accommodate the type of nurse call station with which the monitor is used.

According to still another aspect of the instant invention, there is provided a bed monitor/computer system which allows easy on-site configuration of a monitor to work with different nurses stations. In more particular, the monitor of the instant invention is designed to be reconfigured through the use of a host computer, which obviates the need for internal modifications of monitor parameters through the use of dip switches, rotary dials, etc., which are commonly used in the industry. In the preferred embodiment, a standard computer interface, such as serial interface, is provided as a means for communication between the monitor and a separate host computer. This allows the unit to be readily reprogrammed without risking the exposure of the internal electronic components to the environment.

According to still a further aspect of the instant invention, there is taught hereinafter a software system for providing the monitor with new programming instructions or a new "personality" which will enable it to operate with potentially any plug-compatible nurse call station. In the preferred embodiment, the internal operating logic and various parameters which change the operation of the device to match a particular nurse call station are preferably stored in non-volatile flash-type RAM which is RAM that can be modified on demand through the use of a host computer-to-patient monitor transfer. One obvious advantage of this arrangement is that it eliminates the many problems associated with mechanical configuration switches, such as dip switches and rotary dials, while providing an easy, inexpensive, and reliable way of upgrading or otherwise modifying the functionality of a monitor while it is in the field.

The foregoing has outlined in broad terms the more important features of the invention disclosed herein so that the detailed description that follows may be more clearly understood, and so that the contribution of the instant inventor to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Additionally, the disclosure that follows is intended to cover all alternatives, modifications and equivalents as may be included within the spirit and scope of the invention as defined by the appended claims. Further, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which.

DETAILED DESCRIPTION OF THE INVENTION

Microprocessor-Based Patient Monitor

Figure 1:
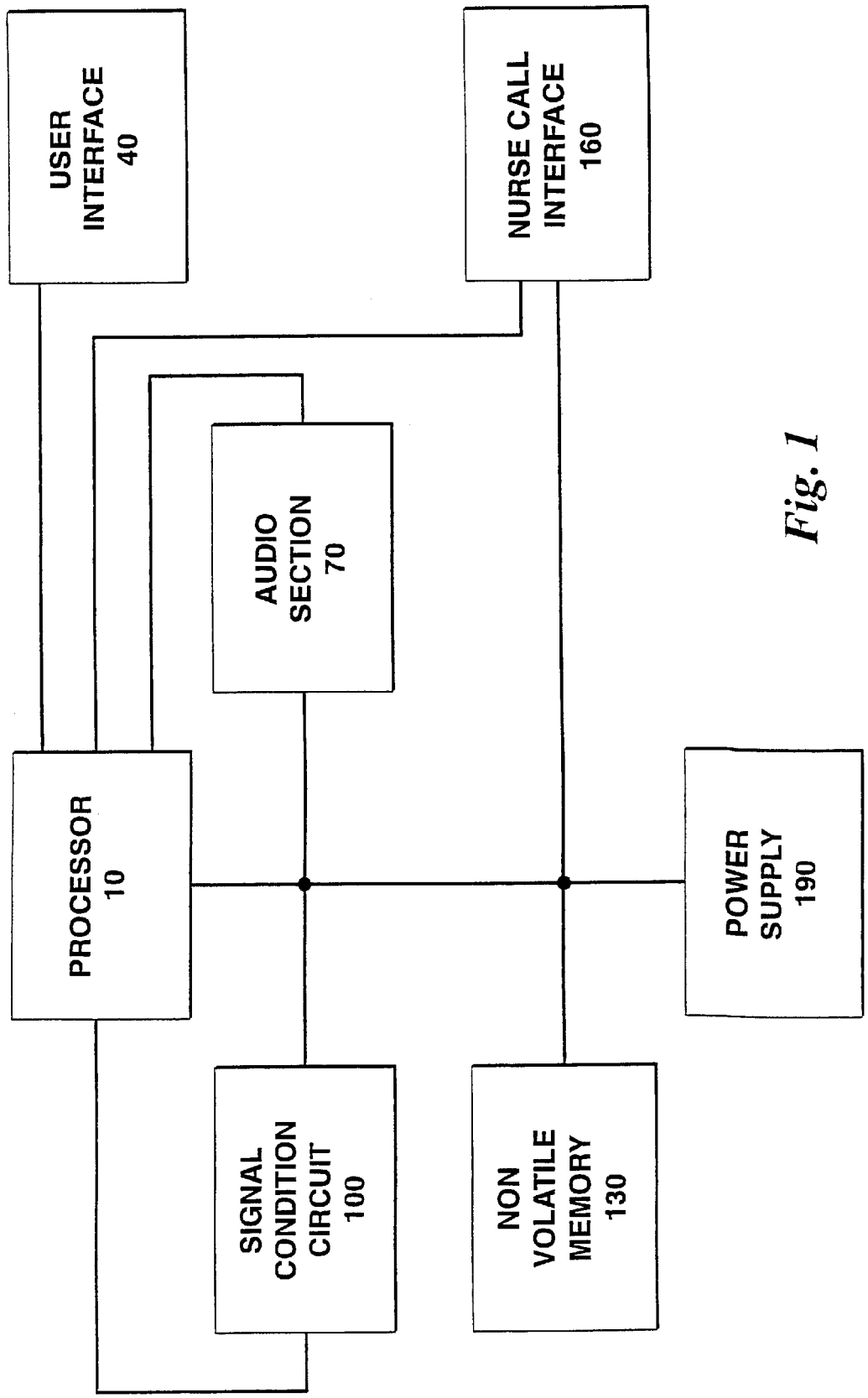
FIG. 1 is a block diagram illustrating a preferred embodiment of the monitor.
Figure 2:
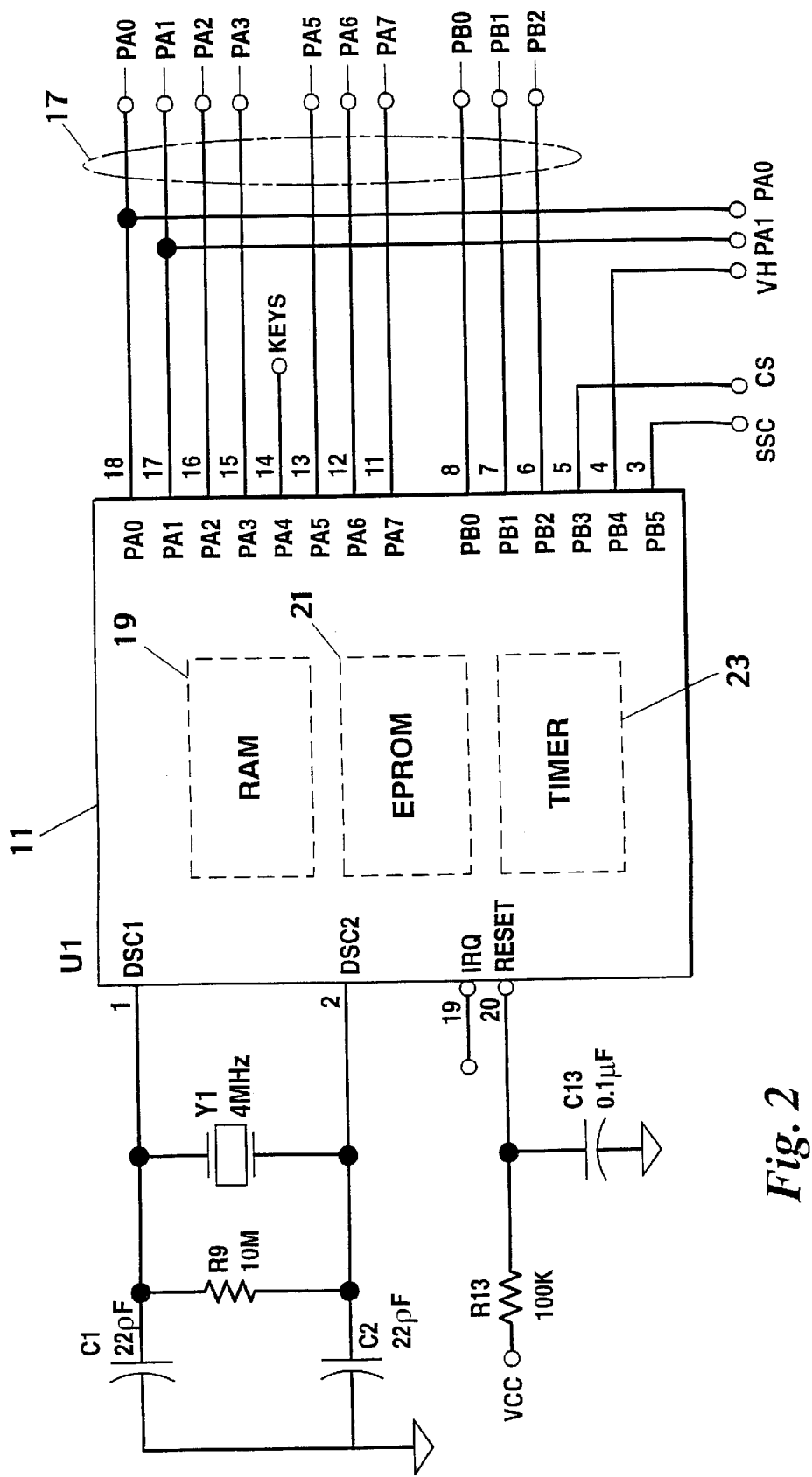
FIG. 2 is a schematic diagram illustrating a portion of a preferred embodiment of the processor of the monitor.
Figure 3:
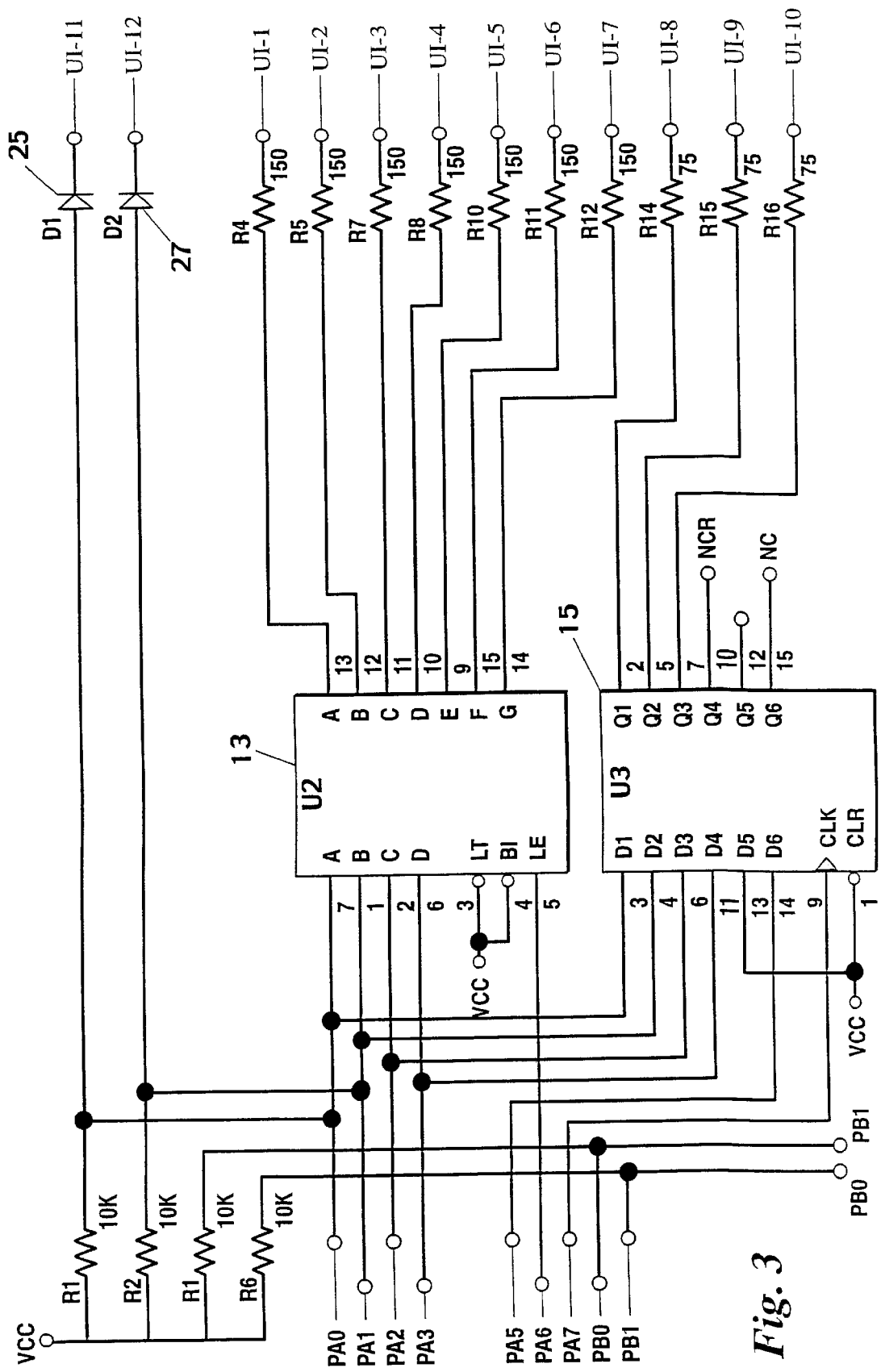
FIG. 3 is a schematic diagram illustrating a portion of a preferred embodiment of the processor of the monitor.

According to a first aspect of the instant invention, there is provided a microprocessor based patient monitor that offers improved functionality in comparison with known control units by introducing added features and improvements in the intuitiveness of the operation. As is illustrated in FIG. 1, a preferred embodiment of the instant monitor hardware has seven functional blocks including a processor 10, a user interface 40, an audio section 70, a signal conditioning circuit 100, a non-volatile memory 130, a nurse call interface 160 and a power supply 190.

As is made clear in FIG. 1, the microprocessor 10 is responsible for various functions within the monitor including managing its user interface 40, communicating with the nurse call interface 160, and controlling the signal condition circuit 100/audio section 70. Additionally, the processor 10 is able to retrieve from and store to non-volatile memory 130 as needed.

As shown in FIGS. 1 through 5, the processor 10 includes a microcontroller 11, a latching display driver 13 and a latch 15. Since the microcontroller 11 is synthesizing the alarm sound in software, it is important to run the microcontroller 11 at its maximum operating speed. The microcontroller 11 preferably has fourteen general purpose I/O pins grouped into a port A and a port B and one interrupt request input IRQ. The pins of the microcontroller 11 are preferably utilized as follows:

Port A Bit 0: via a multifunction bus ("mfb") 17 to D1 of the latch 15, AIN of the latching display driver 13, INC of a volume control 71 in the audio section 70, via a diode 25 to U111 of the user interface 40 and via a resistor R1 to VCC;

Port A Bit 1: via the multifunction bus 17 to D2 of the latch 15, BIN of the latching display device 13 and U/D of the volume control 71, via a diode 27 to UI-12 of the user interface and a pull up resistor R2 to VCC;

Port A Bit 2: via the multifunction bus 17 to D3 of the latch 15 and CIN of the latching display driver 13;

Port A Bit 3: via the multifunction bus 17 to D4 of the latch 15 and BIN of the latching display driver 13;

Port A Bit 4: to Key Input Enable ("KEYS") of the user interface 40;

Port A Bit 5: via the multifunction bus 17 to D6 of the latch 15;

Port A Bit 6: to LE of the latching display driver 13;

Port A Bit 7: to CLK of the latch 15;

Port B Bit 0: to SDA of the non-volatile memory 130 (EEPROM Data), via a resistor R3 to VCC and the power supply 190;

Port B Bit 1: to SCL of the non volatile memory 130 (EEPROM clock), via a resistor R6 to VCC and the power supply 190;

Port B Bit 2: to the nurse call interface 160 (pull out detection);

Port B Bit 3: to CS of the volume control 71 (volume);

Port B Bit 4: to VH of the volume control 71 (audio out);

Port B Bit 5: to the signal condition circuit 100 (mat detection);

IRQ: (Interrupt Request) to the signal condition circuit 100 (mat input);

Reset: to VCC through the time delay R13/C13; and

OSCI & OSC2: to the master clock for the microcontroller 11.

Additionally, the remaining pins of the latching display driver 13 are preferably used as follows:

AOUT: Via a resistor R4 to UI-1 of the user interface 40;
BOUT: Via a resistor R5 to UI-2 of the user interface 40;
COUT: Via a resistor R7 to UI-3 of the user interface 40;
DOUT: Via a resistor R8 to UI-4 of the user interface 40;
EOUT: Via a resistor R10 to UI-5 of the user interface 40;
FOUT: Via a resistor R11 to UI-6 of the user interface 40;
GOUT: Via a resistor R12 to UI-7 of the user interface 40; and
LT and B1: to VCC The remaining pins of the latch 15 are preferably used as follows:

Q1: via a resistor R14 to UI-8 of the user interface 40;
Q2: via a resistor R15 to UI-9 of the user interface 40;
Q3: via a resistor R16 to UI-10 of the user interface 40;
Q4: to the nurse call interface ("NCR") 160;
Q5: unused;
Q6: to the nurse call interface ("NC") 160; and
D5 and CLR: to VCC.

The multifunction bus 17 to D1, 2, 3, 4 and 6 of the latch 15 capitalizes on the bidirectional feature of the microcontroller 11 to create a local data bus. This allows the associated pins PA0, 1, 2, 3 and 5 of the microcontroller 11 to be used for several functions, reducing the total number of I/O pins required and allowing for a smaller, less expensive microcontroller 11 to be used. The multifunction bus 17 sources information for a numeric display 41 via the latching display driver 13, selects annunciators 43 to be illuminated via the latch 15, energizes the nurse call relay K1 via the latch 15, provides up/down information for the programmable volume control 71 and inputs the status of the keypad 45. Operation of the multifunction bus 17 is purely under software control. The microcontroller 11 contains internal RAM 19, EPROM 21, and a Timer 23. One suitable hardware choice for the microcontroller 11 is a Motorola MC68HC705J2, the latching display driver 13 is a Motorola 74HC4511 and the latch 15 is a Motorola 74HC174.

A resistor R13 and capacitor C13 connected between the power source VCC and the RESET port of the microcontroller 11 provide time delay at initialization and a typical clock circuit is connected to the OSC1 and OSC2 ports of the microcontroller 11.

Figure 4:
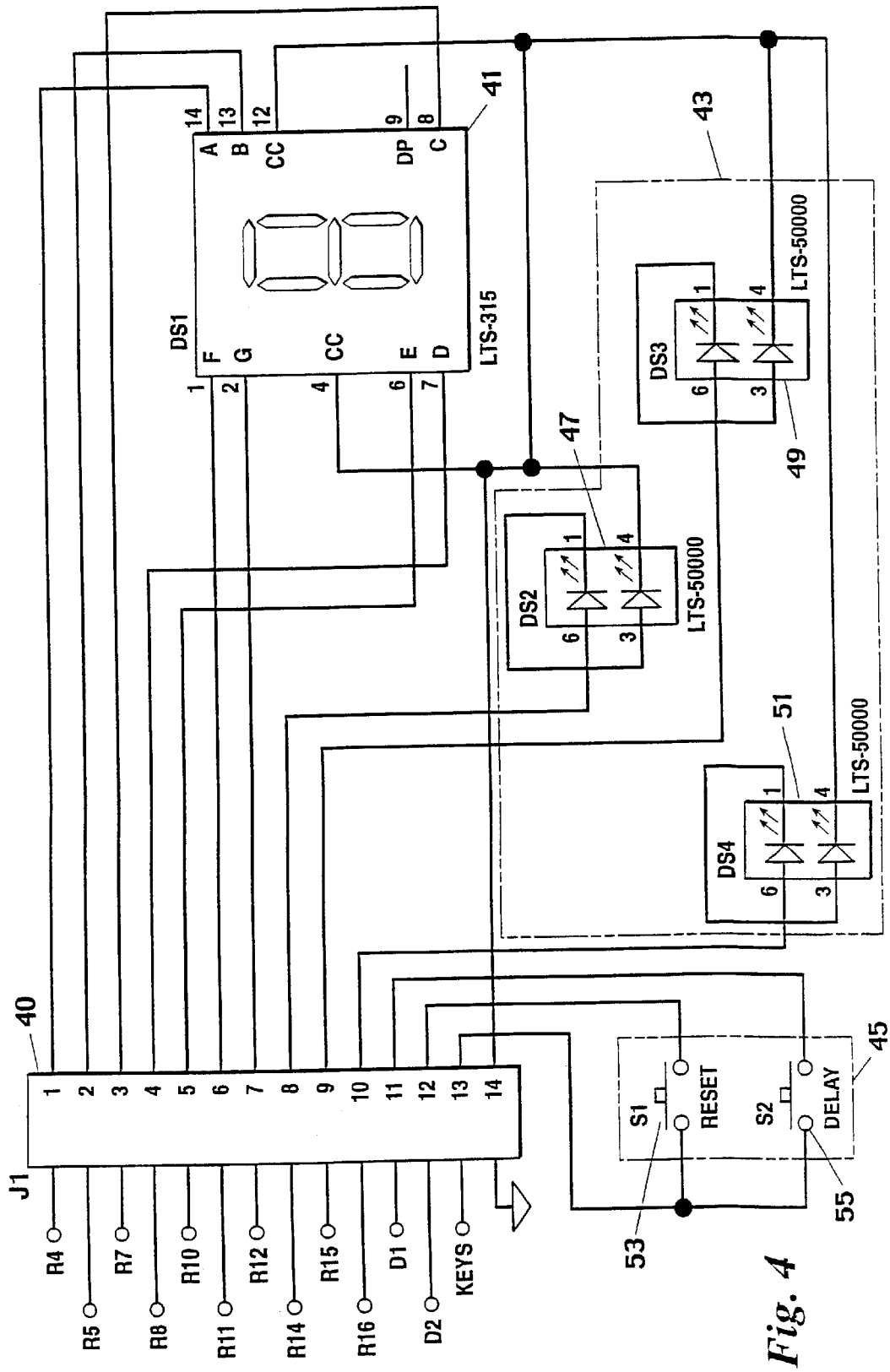
FIG. 4 is a schematic diagram illustrating a preferred embodiment of the user interface of the monitor.

Turning to FIG. 4, the user interface 40 preferably consists of the numeric display 41, an annunciator bank 43 including a HOLD annunciator 47, a MON annunciator 49 and an ALARM annunciator 51 and the keypad 45 including a reset switch 53 and a delay adjust switch 55. Needless to say, many other arrangements of the control switches and displays are possible and are well within the capability of one of ordinary skill in the art to devise.

The numeric display 41 is a seven segment display driven by the latching display driver 13. The preferred latching display driver 13, such as the Motorola 74HC4511, takes Binary Coded Decimal (BCD) in and decodes it into the appropriate segments to display the desired number. The BCD input is provided by A–D carried on PA0 through PA3 of the multifunction bus 17. The information is latched into the latching display driver 13 by Port A Bit 6. The latching operation frees up the multifunction bus 17 for other purposes while maintaining a stable display. The latching display driver 13 provides a blanking function, a totally dark display, by writing a number greater than nine to the BCD input. Four bits of data provide 16 possible combinations (0–15), while only ten combinations are defined in BCD (0–9). The other six combinations (10–15) result in turning off all of the display segments. The numeric display 41 is used to display the seconds of delay which precede an alarm in normal operation of the monitor. In addition, the display 41 is used to show selected options during the local programming mode, as is hereinafter further described in relation to the monitor software. All three annunciators, 47, 49 and 51, are LED's driven by the latching display driver 15. The preferred latching display driver 15, a Motorola 74HC4511, is capable of sourcing 20 milliamps per output 50. No additional drive is necessary to each LED. The driver 15 has a hex latch (six individual D flip/flops with a common clock line). Only five latch outputs are implemented and one of those is unused in the current software. Q1 through Q3 are used for the annunciators 47, 49 and 51, respectively. By using a latch 15 with sufficient drive capability, the latching display driver 15 provides the source current to illuminate each LED and also latches the data so that the annunciators 47, 49 and 51 remain stable while the multifunction bus 17 is used for other purposes. To turn on a particular annunciator 47, 49 or 51, the processor 10 raises the appropriate bit of the multifunction bus 17, D1 for ALARM 47, D2 for MON 49 or D3 for HOLD 51, and then toggles Port A Bit 7 to latch the data. Operating characteristics for each mode are hereinafter described in relation to the monitor software. The reset switch 53 and delay adjust switch 55 are inputted to the processor 10 on bits D2 and D1 of the multifunction bus 17. The two switches 53 and 55 share a common select line so a read of either switch 53 or 55 always reads both switches 53 and 55. To accomplish a read, the processor 10 must make Port A Bit 0 and Port A Bit 1 inputs. The switches 53 and 55 are then read by taking Port A Bit 4 low. The two inputs are pulled up by resistors R1 and R2 and these two bits may be pulled low through diodes D1 and D2 respectively. This can only happen if the appropriate switch 53 or 55 is closed and the key enable line is low.

Figure 5:
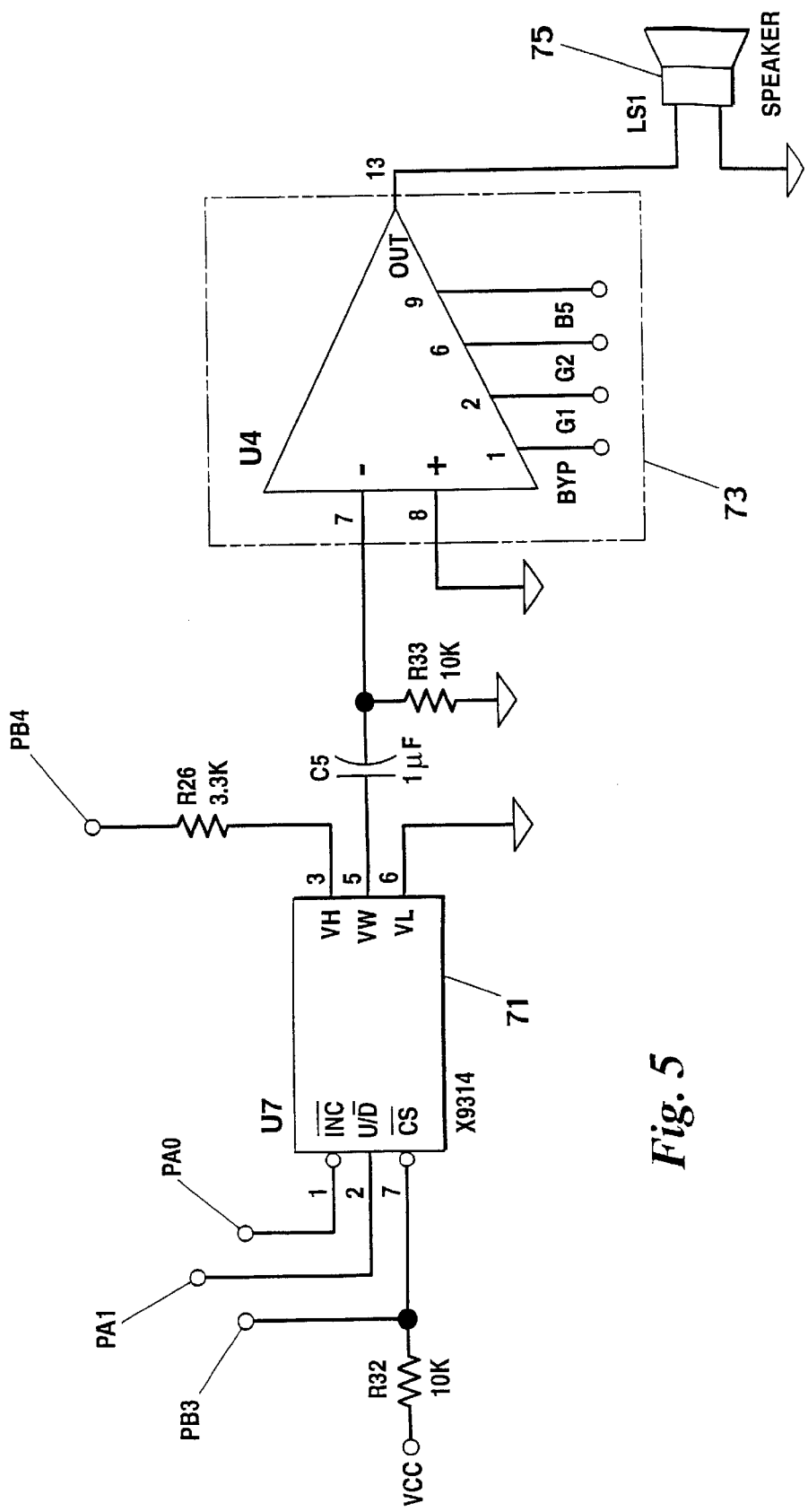
FIG. 5 is a schematic diagram illustrating a preferred embodiment of the audio section of the monitor.

Looking now at FIG. 5, the audio section 70 preferably consists of a programmable volume control 71, a power amplifier 73 and a loudspeaker 75. The audio is a single bit square wave generated by the processor 10 under software control. In a preferred arrangement, the audio signal is divided to the requested volume by the programmable volume control 71, the power amplified to a sufficient level to drive the loudspeaker 75, and converted to audio by the loudspeaker 75. That being said, those of ordinary skill in the art will readily recognize that it is not essential that any particular volume control be used and, indeed, many alternatives are possible and within the scope of the instant invention.

The volume control 71 is preferably a Xicor Corporation X9314 digital potentiometer. This integrated circuit performs the same function as a potentiometer except the wiper position VW is digitally positioned to any one of 32 (i.e., 0–31) possible steps. The circuit is designed such that position zero corresponds to a minimum volume (no sound) and position 31 is maximum volume. To control the volume chip select CS, which is connected to VCC via a pull-up resistor R32, is set low (Port B Bit 3), the up-down pin U/D (mfb D1) is set low to reduce volume or high to increase volume, and the increment-decrement INC pin (mfb D0) is toggled the appropriate number of times to reach the new wiper position.

The multifunction bus 17 is used for the U/D control and for the INC control since these signals have no effect on the chip in the absence of a valid chip select signal. Therefore, using mfb D1 and mfb D2 will not effect the volume when used for other purposes and the chip select signal (active low) is high. The output of the programmable volume control 71 is AC coupled by a resistor R33 and capacitor C5 and directed to the input of the audio power amplifier 73.

The power amplifier is preferably a National Semiconductor LM388 audio amplifier which has adequate drive for the required volume levels and requires relatively few discrete components to produce a viable audio amplifier. It is used in its simplest configuration and directly drives the unit's loudspeaker 75. It preferably has a fixed gain of 20 and a resistor R26 scales the audio appropriately for the desired maximum output level.

The loudspeaker 75 is preferably a simple two inch polycone speaker. However, it should be noted that other arrangements are certainly possible and it is within the ordinary skill of in the art to devise. By way of example only, the loudspeaker element might be a piezoelectric device capable of generating an audible alarm signal. Thus, when the term "loudspeaker" is used hereinafter, that term should be construed in the broadest possible sense to include any device capable of emitting an audible alarm signal under the control of the microprocessor 10. Additionally, when loudspeaker is used herein that term should also be taken to include an associated power amplifier, if one is necessary from the context of its use (as it usually will be). Finally, it should also be noted that it is not an essential element of the instant invention that the loudspeaker 75 be found within the body of the monitor. The speaker 75 could also be mounted externally thereto, and, as an extreme example, might by located in an adjacent hallway or at the nurses station.

Figure 6:
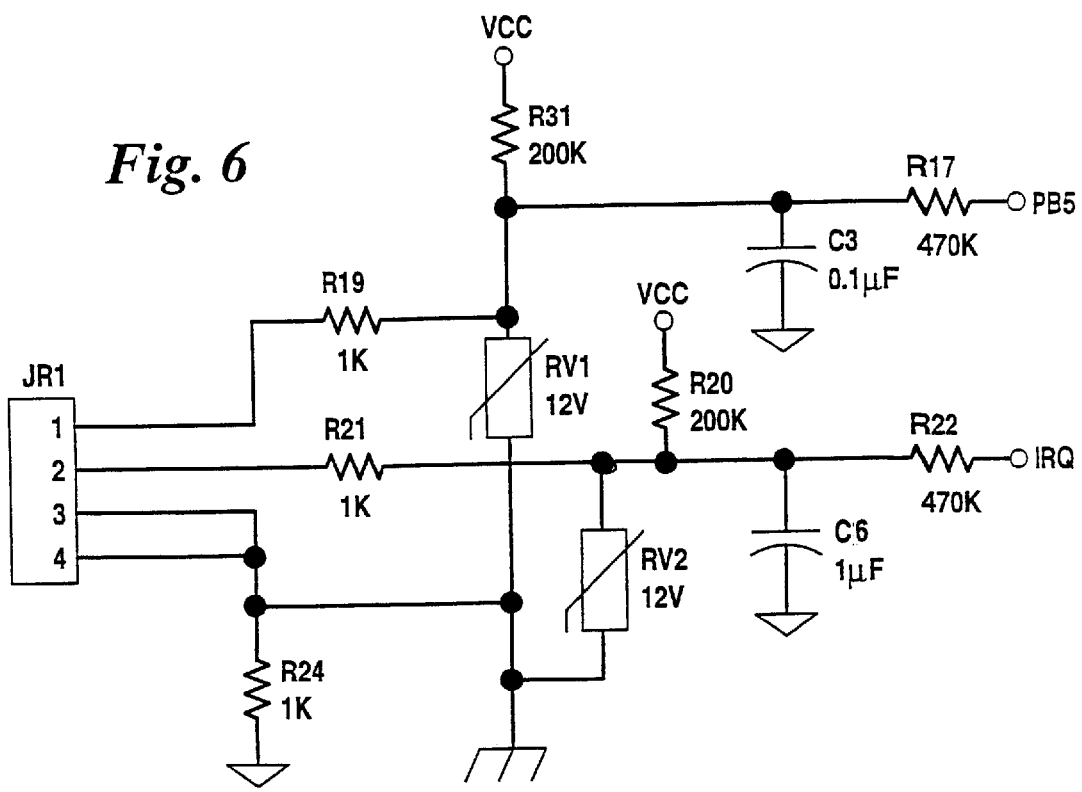
FIG. 6 is a schematic diagram illustrating a preferred embodiment of the signal condition circuit of the monitor.

The signal conditioning circuit 100, shown in detail in FIG. 6, filters noise from the mat inputs JR1—1 and 2 and provides a reasonable degree of protection to the monitor from static discharge. Filtering at one input JR1–2 is accomplished by a single RC circuit including resistors R20 and R21 and a capacitor C6 and at the other input JR1—1 by a simple RC circuit including resistors R19 and R31 and a capacitor C3. This eliminates some noise and assists in increasing the immunity from static discharge. A static discharge to the monitor passes through the RC filters and is then clamped by surge limiting devices, RV1 and RV2 of FIG. 6. The combination of the first input components R20, R21, C6 and RV2 and the second input components R19, R31, C3 and RV1 should provide static protection far in excess of known monitors.

Figure 7:
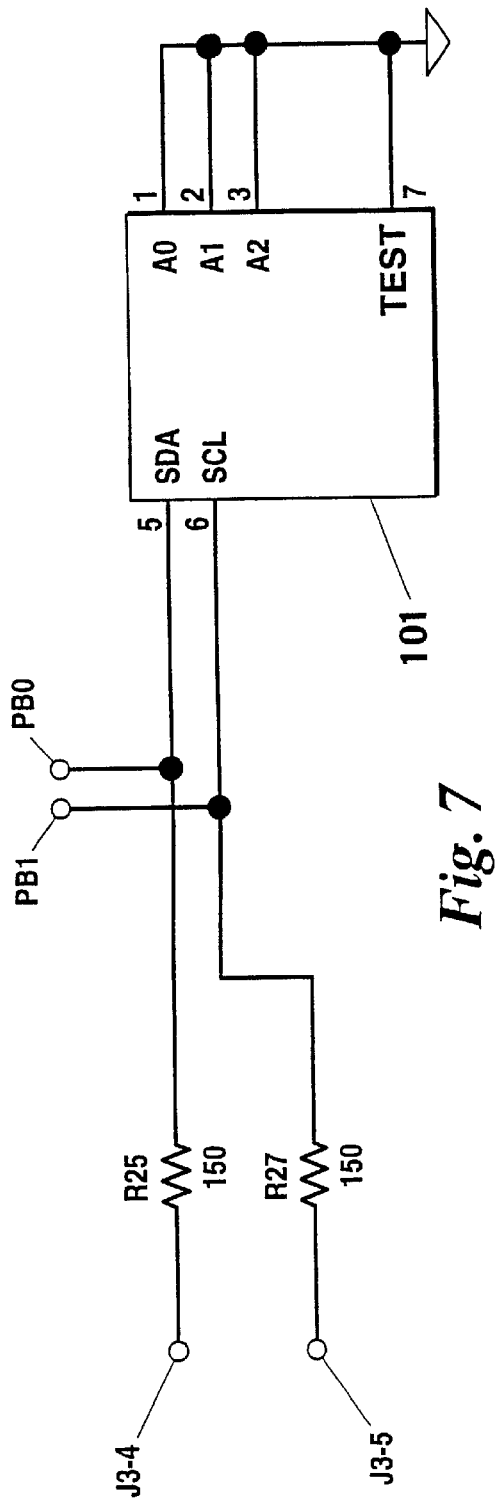
FIG. 7 is a schematic diagram illustrating a preferred embodiment of the non-volatile memory of the monitor.
Figure 15:
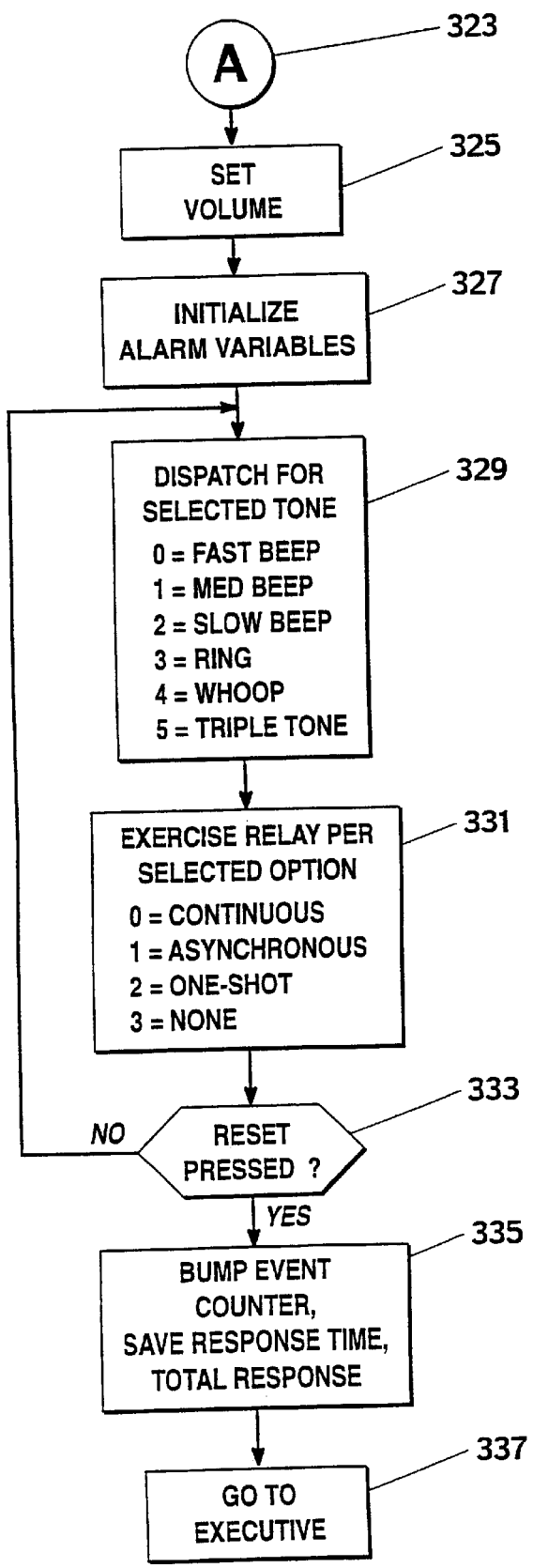
FIG. 15 is a flow diagram of another portion of the alarm mode routine of the monitor.

The non-volatile memory 130 illustrated in FIG. 7 includes a 1 Kbit (128×8) electrically erasable programmable read only memory EEPROM 101. It is connected via resistors R25 and R27 to the power supply interface connections J3–4 and J3–5. The actual IC chip is preferably a Microchip X24LC01 which uses a two wire serial interface to communicate with the processor 10. The interface is based on the I2C bus which has become the predominant standard for low cost inter-chip communications (i.e., "Inter-IC" bus, which is a standard means of providing a two-wire communication link between integrated circuits). Detailed information on the chip and the I2C bus may be found in the Microchip Nonvolatile Memory Products databook. The EEPROM 101 is used to store operating characteristics, usage information and device specific information such as a repair log and unit serial number. The operating characteristics are defined, in part, by a collection of user-modifiable parameters that control various aspects of the monitor's operations, including, for example, the type of alarm tone (e.g., FIG. 15, item 329), the relay action, the hold time delay, and the volume of the alarms. These memory locations may be modified either through use of the front panel control switches or, as hereinafter described, via a computer program that is executing on a remote host connected to the monitor via an electronic interface, such as a serial port. Usage information might consist, by way of example only, of an hour meter which logs total hours of use of the monitor, the total time alarming, the total number of alarms, the response time to the last alarm, and/or the date and time of past alarms (the calendar date and time being provided by, for example, a date/time chip 595 of the sort illustrated in FIG. 22).

Downloading usage information to a host computer allows a number of diagnostic statistics to be calculated, including the "average time to respond". This information is preferably only be written by the monitor, and read only to an inquiring host computer. Read only status is purely a software function of the host. Device specific information would typically not be used by the monitor and is never written to or read by the monitor. It is preferably written only at the time of manufacture or time of repair by an external host computer. The information is intended for use by the factory, a repair station, or a facilities biomedical staff and might include, for example, the date of the last ten repairs and corresponding work order numbers and the unit's serial number.

Figure 8:
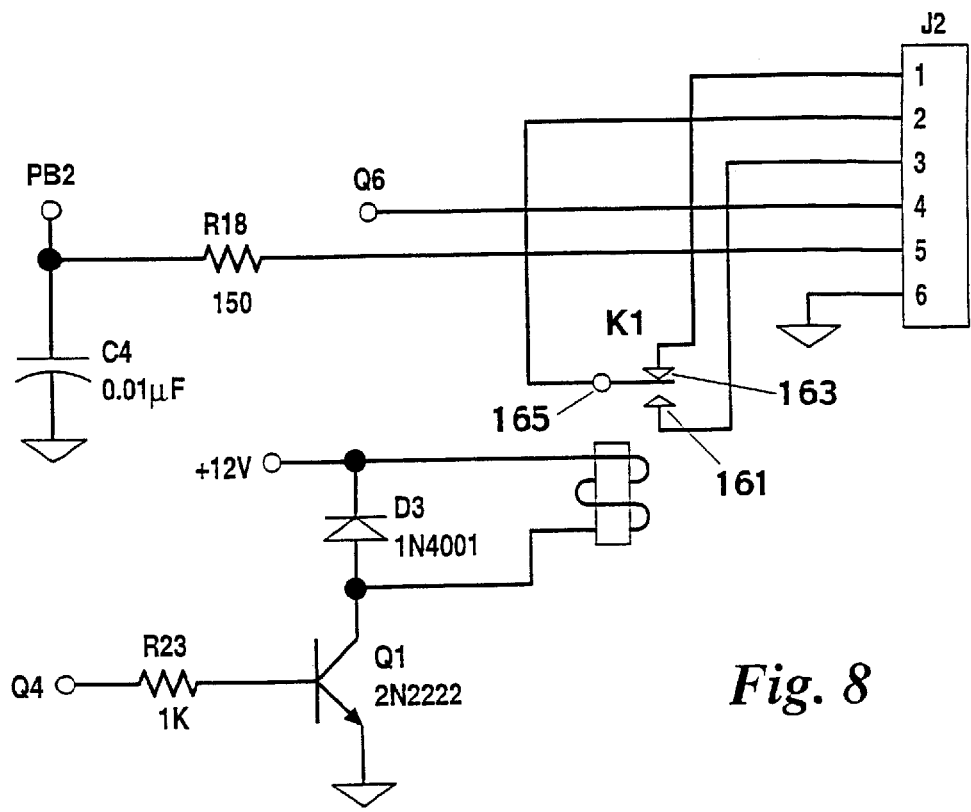
FIG. 8 is a schematic diagram illustrating a preferred embodiment of the nurse call interface of the monitor.

Turning now to FIG. 8, the nurse call interface 160 uses a relay K1 to provide isolation between the monitor circuitry and the nurse call system. A normally open contact 161, a normally closed contact 163 and a common contact 165 of the relay K1 are connected to a connector J2. The nurse call cord (not shown) plugs into this connector J2 and would typically be an RJ-45 or similar connector. Since there is always a potential for inadvertent disconnection of a connector J2, two additional pins J2–4 and 5 are used in the connector J2 to provide a continuity loop. By monitoring this loop, the processor 10 can detect a pulled-out nurse call cord. If this condition is detected, a distinct in-room alarm is sounded. Pull-out protection may be disabled via the profile stored in the nonvolatile memory 130 when the system is used in a facility without a nurse call system or in a home. The relay K1 is energized in the non-alarming state. This effectively reverses the contacts 161 and 163 so that the normally open contact 161 appears to be normally closed and vice versa. Thus, a nurse call is issued whenever power is interrupted to the monitor. This provides a fail safe on the power supply 190 and its interconnects. A single RC filter consisting of a resistor R18 and a capacitor C4 provides static protection for the processor 10. The relay K1 is turned on by the transistor Q1 via a current limiting resistor R23 and a diode D3 which absorbs the inductive kick which occurs when the relay K1 is de-energized.

Figure 9:
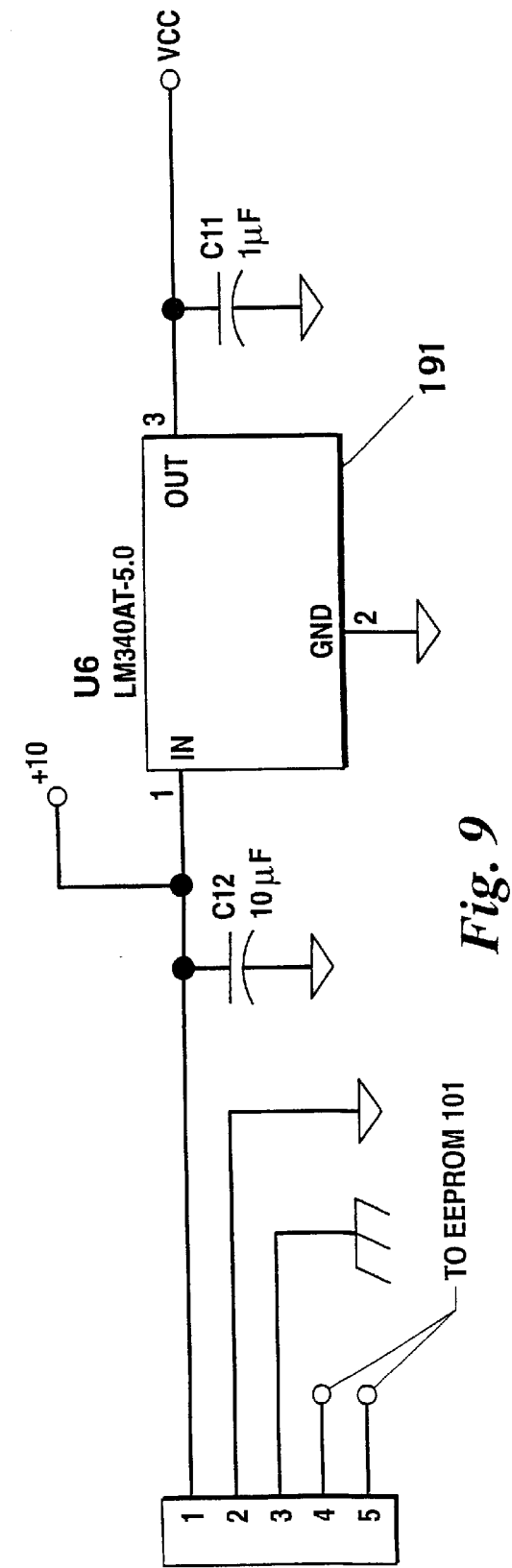
FIG. 9 is a schematic diagram of a preferred embodiment of the power supply of the monitor.

As shown in FIG. 9, the power supply 190 includes an external connector J3. The connector J3 includes a transformer (not shown) connected between two pins J3–1 and J3–2 of the connector. Power VCC is brought into the monitor through a voltage regulator 191 connected to the first connector pin J3–1. Two additional pins J3–4 and 5 of this connector J3 are used for the read/write interface of the external EEPROM 101. Filter capacitors C11 and C12 are preferably connected on either side of the voltage regulator 191.

Monitor Front Panel Control Functions

The internal software allows the monitor to perform a variety of functions. As illustrated in FIG. 4, the user interface 40 includes inputs allowing a user to modify control unit actions via the reset button 53 and to adjust the delay via the delay adjust button 55 and outputs for controlling operation of the 0 through 9 numeric display 41, the status annunciators 43 and various aural signals.

An idle mode (HOLD), which is active when the monitor is not monitoring, enables automatic advancement to the monitor mode, manual override for immediate advancement to the monitor mode, adjustment of the delay time, aural indications of any unsafe conditions and logging of hours in use. The monitor mode (MON) enables monitoring of the patient for activity within the bed which could be a precursor for a bed evacuation, adjustment of the delay time, manual return to the idle mode (HOLD), automatic advancement to the alarm mode (ALARM), aural indications of any unsafe hardware conditions and logging of hours in use. The alarm mode (ALARM) enables generation of a nurse call through the nurse call system 160, aural in-room alarm, manual return to the idle mode (HOLD) and logging of response time and total alarm time. A program mode enables the user to customize the features of the monitor and to update the non-volatile memory 130 with user selected parameters.

All functions which utilize the user interface 40 are consistent with the nomenclature which the user sees on the labels of the buttons 53 and 55 and on the numeric display 41. For example, any features which use the reset button 53 have an intuitive connection to the word "reset". Likewise, the delay adjust button 55, which preferably features a triangle pointing up, causes an upward adjustment in the numeric display 41 with appropriate roll over at a maximum value.

Internal Software/Logic Functions

Figure 10:
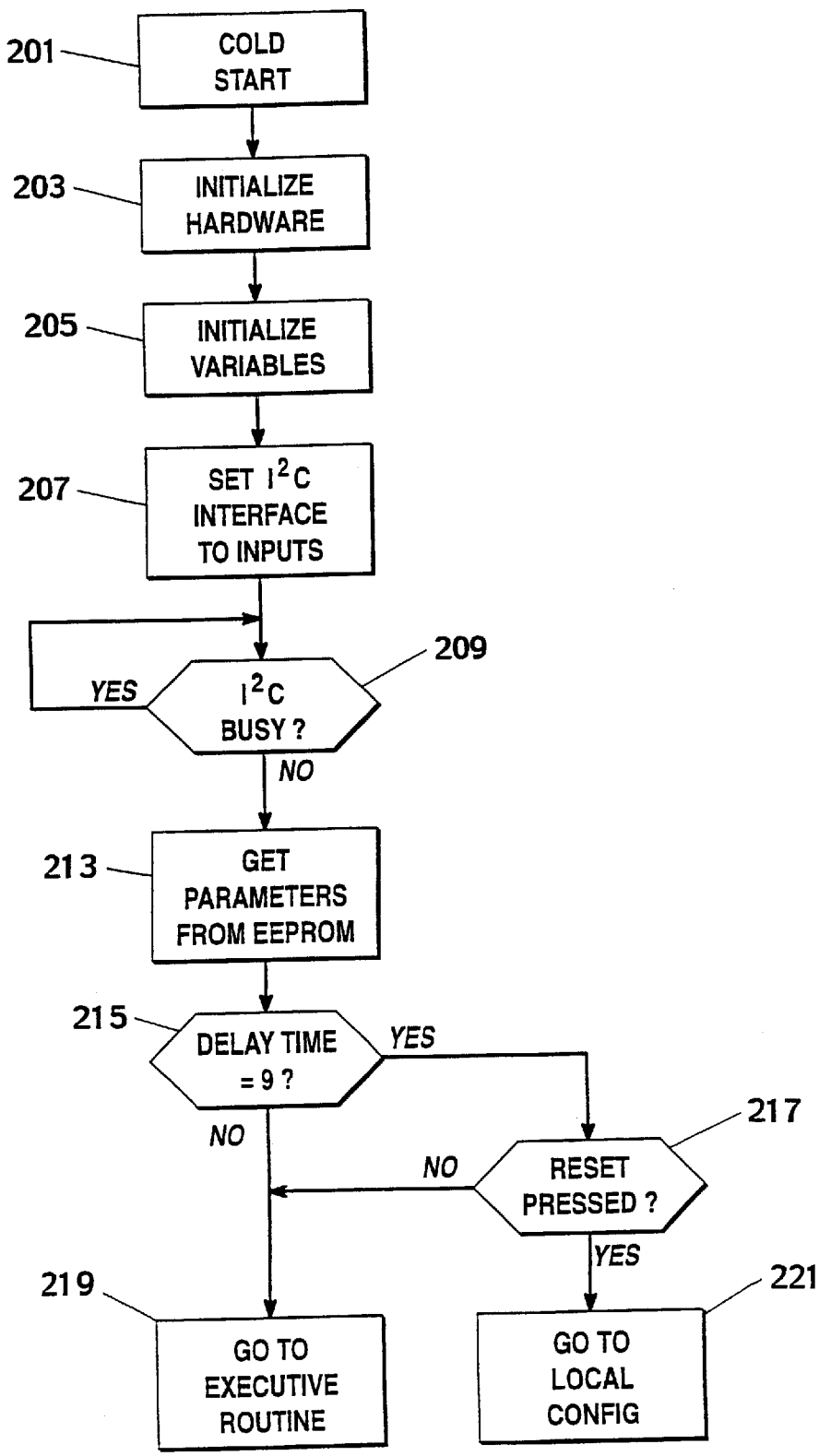
FIG. 10 is a flow diagram illustrating a preferred embodiment of a cold start routine of the monitor.

FIG. 10 illustrates the main steps that are executed within the monitor as part of a power-up (i.e., cold start) sequence. In the preferred embodiment, a cold start 201 will cause the processor 10 to automatically enter into the HOLD mode as part of step 201. Then, the system initialize hardware 203 and variables 205, after which it will then set the I2C interface to inputs 207 to determine whether the interface is already being used, for example to change the programs in the EEPROM 101. An inquiry is then made as to whether the I2C is busy 209. If the response to this inquiry is "YES," then the inquiry is repeated until the response is "NO." If a "NO" response is received, the system proceeds to recall parameters stored previously within EEPROM 213. The system will next inquire as to whether the delay time equals nine (step 215). If the response to this inquiry is "YES," the system will next inquire as to whether the reset is pressed 217. If the response to either the inquiry as to whether the delay time equals nine 215 or whether the reset is pressed 217 is "NO," then the system proceeds to go to executive routine 219. If the response to the inquiry as to whether the reset is pressed 217 is "YES," the system proceeds to go to local configuration 221.

Figure 11:
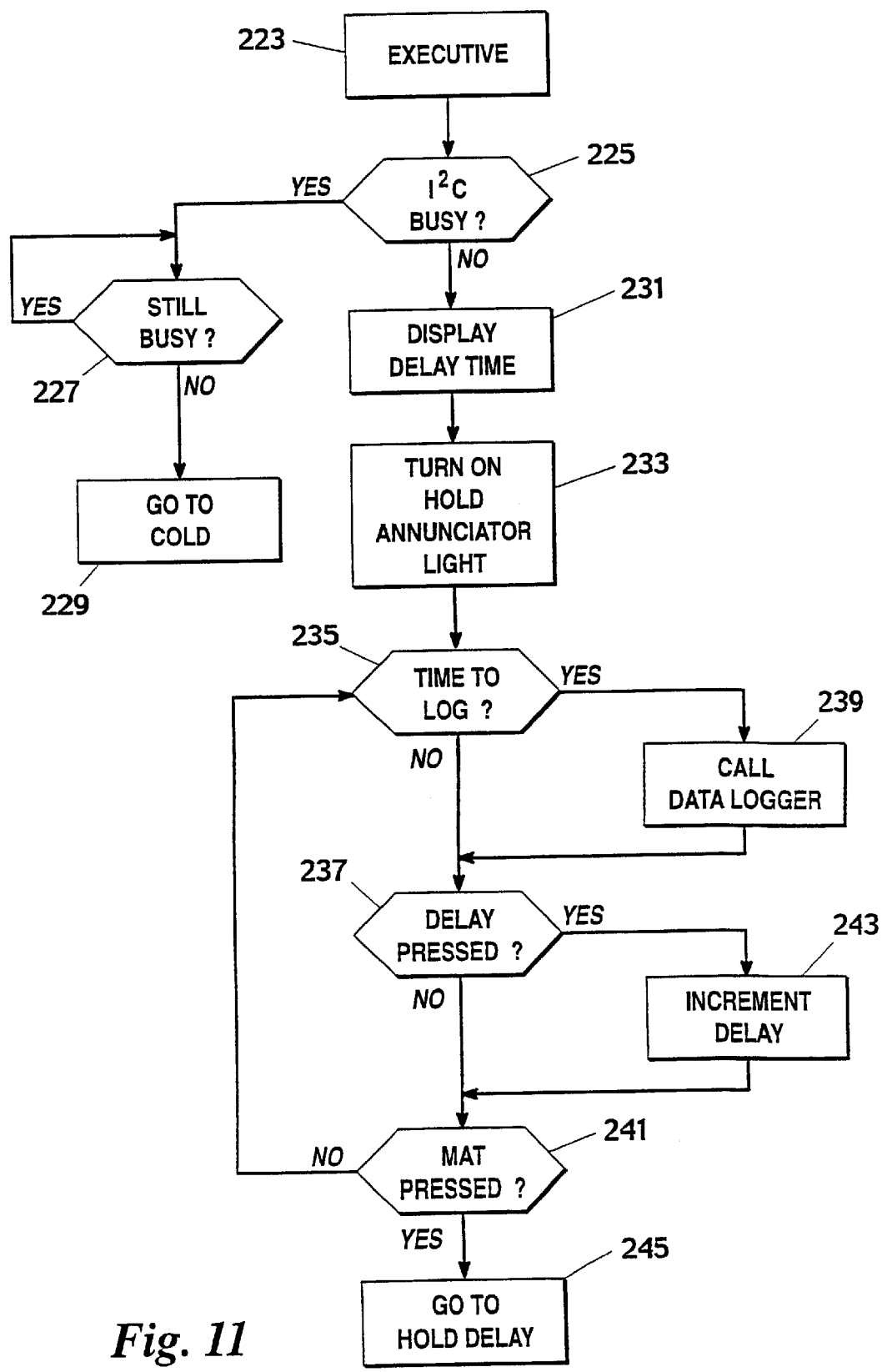
FIG. 11 is a flow diagram illustrating a preferred embodiment of the executive routine of the monitor.

As is illustrated in FIG. 11, if the system has gone into executive 223 mode, the system will again inquire as to whether the I2C is busy 225. If the response to this inquiry is "YES," the system will continue to inquire as to whether the I2C bus is still busy 227. As long as the response to this inquiry is "YES," the inquiry continues. If the response to the inquiry as to whether the I2C bus is still busy 227 is "NO," then the system will go to cold 229 and resume from the cold start 201 as shown in FIG. 10. If, however, on inquiry as to whether I2C is busy 225 the response is "NO," the system proceeds to display delay time 231 on the display 41 and will turn on hold annunciator light 233 which is an indication to the caregiver that there is no weight on the mat used to monitor the patient's presence. The system then inquires as to whether it is time to log (step 235). In the preferred embodiment, every six minutes or ⅒th of an hour the system will log the lapse of an increment so as to maintain a record of total hours of use of the monitor. If six minutes have not elapsed, the response to the inquiry is "NO" and the system proceeds to inquire as to whether the delay adjust switch is pressed 237. If six minutes have elapsed, the response to the inquiry as to whether it is time to log 235 is "YES" and the system will proceed to call data logger 239 so as to register this increment. The system then continues to the delay adjust switch pressed inquiry 237 until another six minute interval has elapsed and the call data logger 239 is again cycled. If the response to the inquiry as to whether the delay adjust switch is pressed 237 is "NO," the system proceeds to inquire as to whether the mat is pressed 241. If the response to the inquiry as to whether the delay adjust switch is pressed 237 is "YES," the system proceeds to increment delay 243 by stepping to the next of the nine increments available for delay as hereinbefore discussed and then inquires as to whether the mat is pressed 241. If the response to the mat pressed inquiry 241 is "NO," the system will recycle to the time to log inquiry 235 and continue the process until the response to the mat pressed inquiry 241 is "YES," indicating that a patient is on the sensing mat. If the response to this inquiry is "YES," the system then proceeds to go to hold delay 245.

Figure 12:
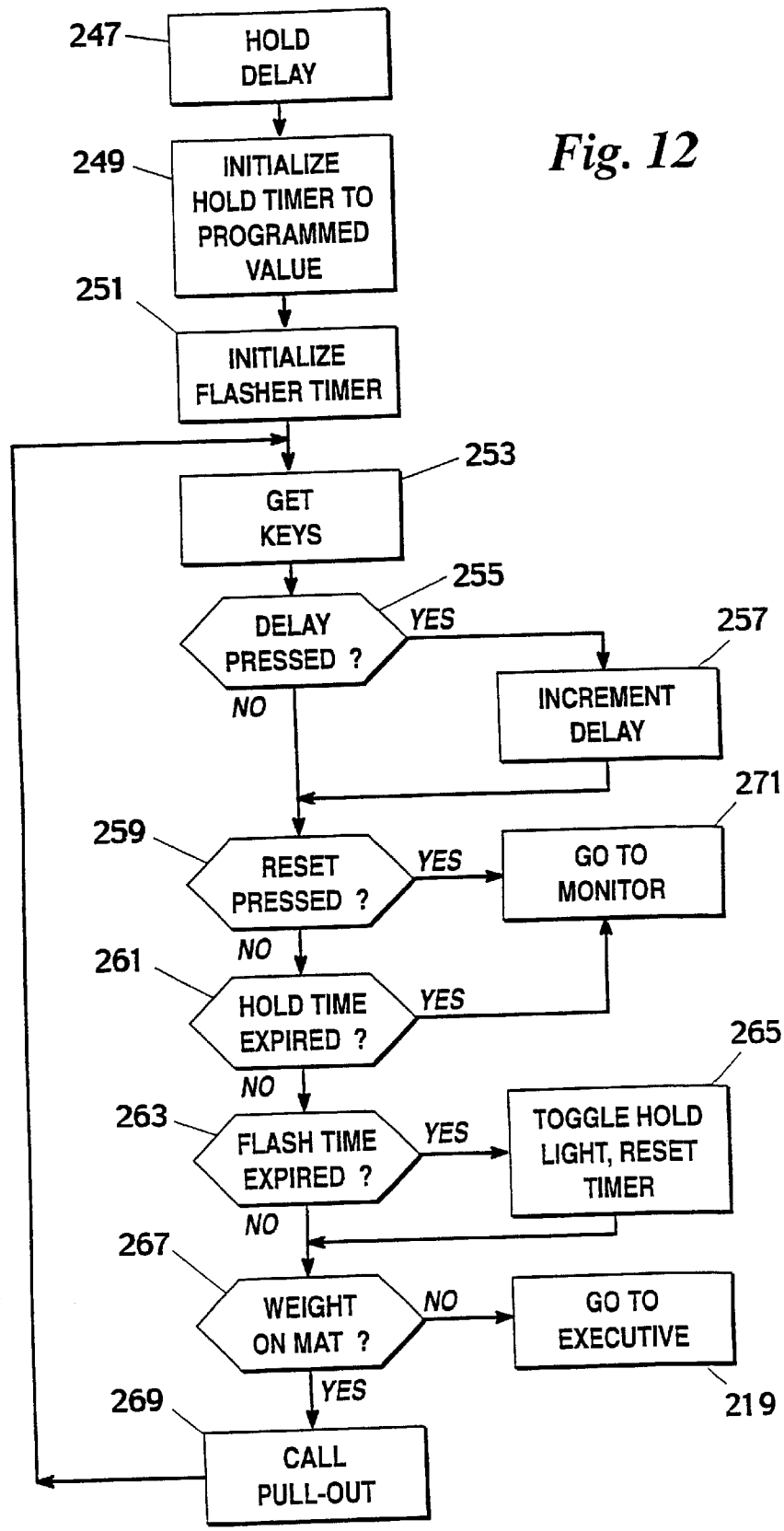
FIG. 12 is a flow diagram illustrating a preferred embodiment of the hold mode routine of the monitor.

Turning now to FIG. 12, representing the transient condition between the hold mode 201 and the monitor mode 273, when the monitor is at hold delay 247, the system will initialize hold timer to program value 249. Generally, the hold timer will permit selection by the caregiver of from 1 to 20 seconds as the interval that the patient's weight must be on the sensing mat before monitoring of the patient's presence is initiated. In the preferred embodiment described herein, this available time interval is in a range of 1 to 9 seconds. The system then proceeds to initialize flasher timer 251. The flasher timer establishes the flash interval for the attenuator indicating that a patient's weight is on the sensing mat. With the timers initialized, the system proceeds to get keys 253 by examining the switches 53 and 55 of the keypad 45. Inquiry is first made as to whether the caregiver has operated the delay adjust 255. A "YES" response indicating that the delay adjust switch 55 is depressed will result in an increment change 257. If the response to the delay adjust inquiry 255 is "NO" or the increment change 257 is made, the system continues on to inquire as to whether the reset is pressed 259. If the response to this inquiry is "NO," the system proceeds to inquire as to whether the hold time is expired 261. If the response to this inquiry is "NO," the system inquires as to whether the flash time has expired 263. If the flash time has expired, providing a YES response, the system will toggle the hold light and reset the timer 265. If the flash time has not expired or has been reset, the system will proceed to inquire as to whether there is a weight on the mat 267. If the response to this inquiry is "NO," the system will go to executive 219, returning to the loop illustrated in FIG. 11. If the response to the weight on mat inquiry 267 is "YES," the system will perform a pullout check 269 to determine if there is an improper connection in the system. After performing the pullout check 269, the system will return to the get keys step 253 of the hold delay loop 247. If, in the operation of the hold delay loop 247, the response to the reset pressed inquiry 259 or the hold time expired inquiry 261 is "YES," then the system will go to monitor 271, as will hereinafter be described.

Preferably, the HOLD mode 235 is characterized by a continuous hold indicator 47 and the number of seconds of delay time is displayed on the numeric display 41. The nurse call relay K1 is energized (non-alarming state). There is no testing of the sensor validation input, there is no pull-out detection, and the keypad 45 is monitored at least 20 times per second except during tone generation. Upon pressing the delay adjust button 55, the delay is bumped by one second and the display 41 is updated with the new delay time. After nine seconds, the delay time resets to one second. If the reset button 53 is pressed, a ½ second tone at 1 kHz is generated. Software exits this loop and enters the pre-monitor phase of the monitor mode MON when weight is detected on the mat (IRQ goes low). During the hold mode HOLD, logging of hours in use occurs every 1/10th of an hour (six minutes).

Figure 13:
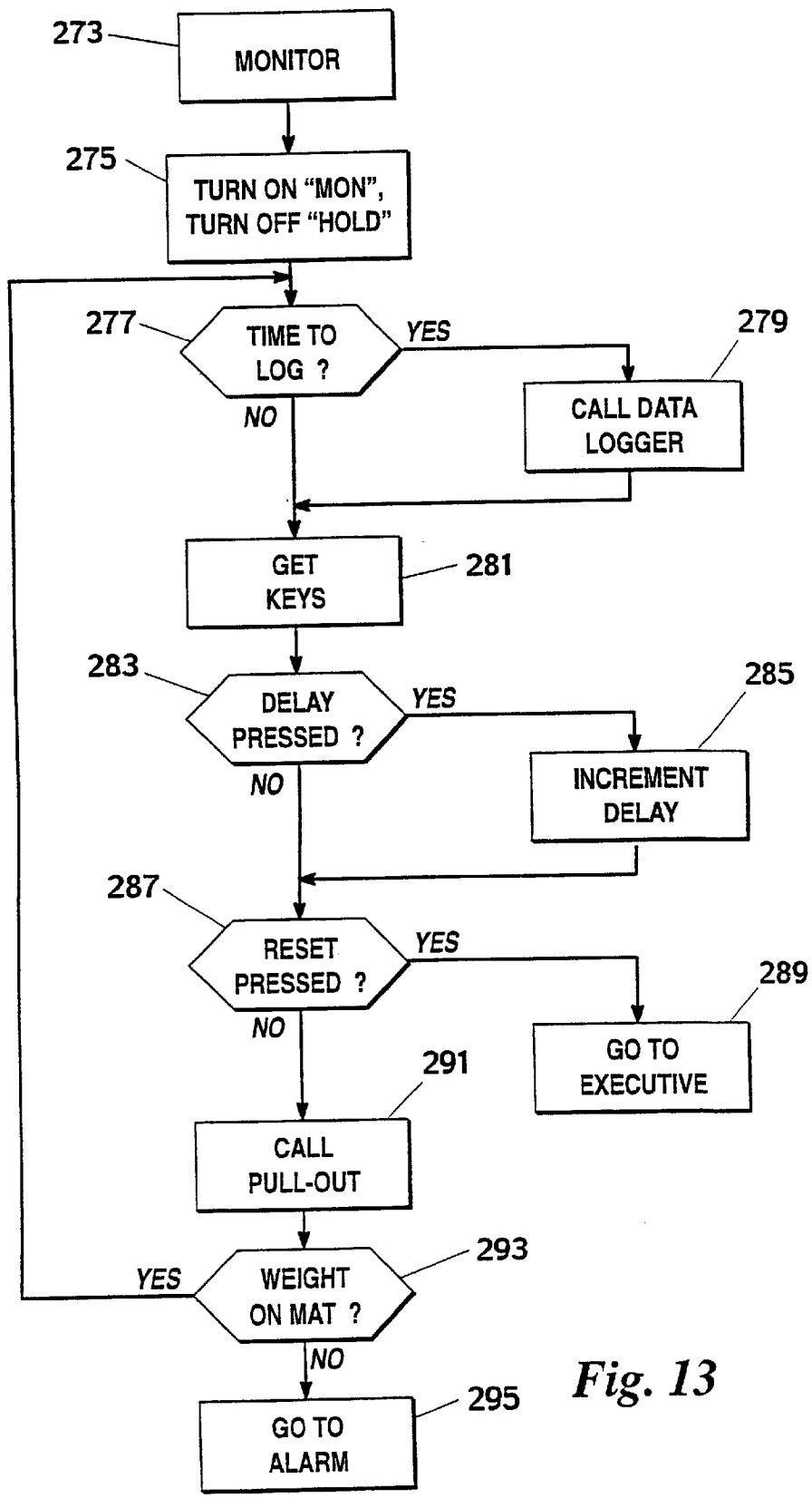
FIG. 13 is a flow diagram illustrating a preferred embodiment of the monitor routine of the monitor.

The main monitor routine is illustrated in FIG. 13. When the system goes to monitor 273, it will change the annunciator condition by turning on MON and turning off HOLD 275. Thus, the HOLD annunciator 47 will be de-energized and the monitor annunciator 49 energized. The system will then inquire as to whether it is time to log 277, as has been hereinbefore explained. If the response to this inquiry is "YES," then the system will call data logger 279 to log the expiration of the six minute increment. If the answer to the inquiry as to time to log 277 is "NO," or if an increment has been logged, the system will proceed to a get keys status 281. The system will inquire as to whether the delay adjust switch is pressed 283. If the response to this inquiry is "YES," an increment change 285 will be made in the time delay. If the response to the delay adjust inquiry 283 is "NO" or the increment change 285 has been made, the system will proceed to inquire as to whether the reset is pressed 287. If the response to this inquiry is "YES," the system will go to executive 289 and perform the loop illustrated in FIG. 11. If the response to the reset pressed inquiry 287 is "NO," the system will proceed to call pull-out 291 to determine whether there is an electrical connection failure in the system. The system then inquires as to whether there is a weight on the mat 293. If the response to this inquiry is "YES," the system will return to the time to log step 277 of the monitor loop 273. If the response to the inquiry as to weight on the mat 293 is "NO," the system will proceed to go to alarm 295.

In a preferred arrangement, the monitor mode 273 has a transient pre-monitor phase shown in FIG. 12 and a steady-state monitor phase shown in FIG. 13. The pre-monitor state is characterized by a flashing hold indicator 47. The LED flash period is 0.2 seconds on and 0.2 seconds off. During the pre-monitor phase, the nurse call relay K1 is energized (non-alarming state), nurse call pull-out protection is active, the sensor input is validated, the numeric display 41 continues to display delay time, and the keypad 45 is polled at least 20 times per second. If the software detects an improperly inserted nurse call connector, a tone will be generated, preferably sixteen cycles of 400 Hz followed by 42 msec of silence, repeated four times, followed by a minimum of 320 msec of silence before repeating the entire process. Pressing the delay adjust button 55 will increment the delay time one second up to a maximum of nine seconds. The delay time then resets to one second. The numeric display 41 is updated with each change in the delay time. Pressing the reset button 53 will cause the monitor to immediately proceed to the monitor phase 273. This mode expires after a programmable hold time. The hold time defaults to ten seconds but may be programmed by the user for any time from 1 to 10 seconds. Upon expiration of the hold time or upon pressing the reset button 53, the software advances to the monitor phase 273. The software will return to the hold mode 247 if weight is removed from the mat prior to entering the monitor phase 273.

Preferably, the monitor phase of the monitor mode 273 is characterized by a solid monitor status indicator 49. During this phase, the sensor is monitored for weight on mat, the nurse call relay K1 is energized (non-alarming state), nurse call pull-out protection is active, the numeric display 41 continues to display the delay time, and the keypad 45 is polled at least 20 times per second. If an improperly inserted nurse call cord is detected, the unit will sound an alarm as described in the pre-monitor phase. Pressing the delay adjust button 55 will advance the delay time one second up to a maximum of nine seconds. The delay time then resets to one second. The numeric display 41 is updated with each change in the delay time. Pressing the reset button 53 will return the software to the hold mode 247, allowing removal of the patient from the bed. Since there must be weight on the mat to be in this mode 247, the hold mode 247 will automatically advance to the pre-monitor phase of the monitor mode 273. To improve functionality, the hold time will temporarily be set to 25 seconds when this path is taken to allow sufficient time to remove the patient from bed. If weight is removed from the mat, the software advances to the pre-alarm phase of the alarm mode. The parameter "hours in use" is preferably logged/incremented every 1/10th of an hour.

Figure 14:
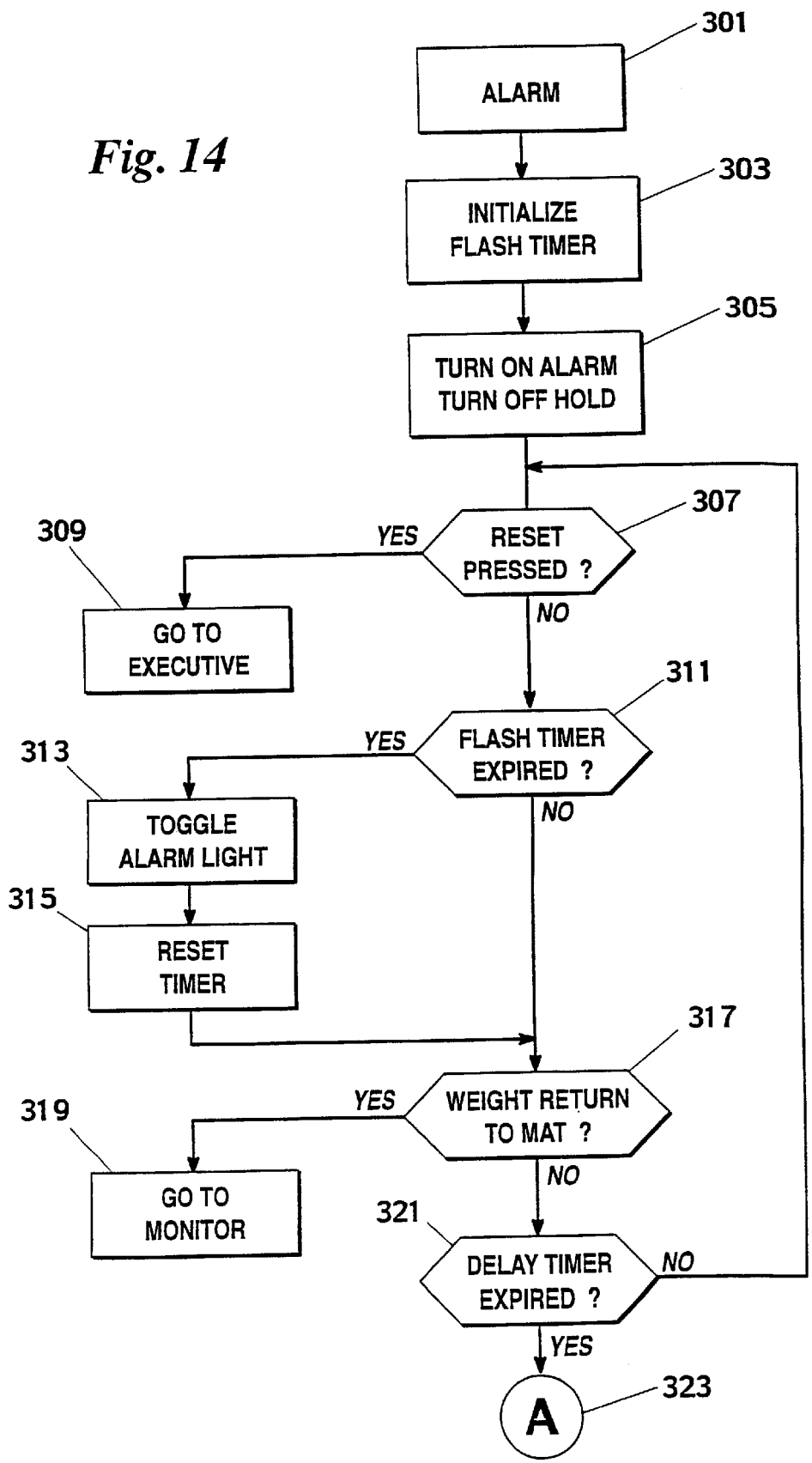
FIG. 14 is a flow diagram illustrating a preferred embodiment of a portion of the alarm mode of the monitor.

The alarm mode 301 illustrated in FIG. 14 consists of a transient re-alarm phase and a steady state alarm phase. The pre-alarm phase is characterized by a flashing alarm indicator 51. The flash period is 0.2 seconds on and 0.2 seconds off. During the pre-alarm phase the nurse call relay K1 is energized (non-alarming state), the mat input is monitored, and the keypad 45 is polled at least 20 times per second. Returning weight to the mat will cause the software to return to the monitor mode 273. Pressing the delay adjust button 55 has no effect. Pressing the reset button 53 will return the software to the hold mode 247. Since this mode 247 is only active with weight off the mat, the monitor will remain in hold upon returning to the hold mode 247. This mode 247 expires after the number of seconds displayed in the numeric display 41 and then enters the alarm phase.

The alarm phase of the alarm mode 301 is characterized by a solid ALARM indicator 51 and an audible alarm. During this mode the nurse call relay K1 is operated in accordance with a pre-programmed protocol and the keypad 45 is preferably polled at least 20 times per second. Pressing the delay adjust button 55 has no effect. The audible alarm will continue to sound until the reset button 53 is pressed, returning the unit to the hold mode 247. The alarm preferably provides one of six possible user selectable alarms (see, for example, 329) including a 1 kHz beep in intervals of 0.5 seconds on and 0.5 seconds off, a 1 kHz beep in intervals of 0.25 seconds on and 0.25 seconds off, a 1 kHz beep in intervals of 1 second on and 1 second off, 16 cycles at 400 Hz followed by 18 cycles at 440 Hz repeated 12 times followed by one second of silence, a rising whoop or a stepped alarm providing four alarms at 320 Hz in intervals of 28 cycles and 28 cycles off, four alarms at 392 Hz in intervals of 32 cycles on and 32 cycles off, four alarms at 277 Hz intervals of 24 cycles on and 24 cycles off with ½ second of silence. It is also possible to have no audible alarm. The nurse call relay K1 has three possible operating modes to accommodate various nurse call systems including continuous closure, one-shot and asynchronous 331. At the termination of the ALARM mode 301, the response time is written to the EEPROM 101, the stored number of alarms is bumped by one and rewritten to the EEPROM 101 and the current response time is added to the total alarm time and the EEPROM 101 is updated with the new value.

In the alarm mode 301 the system will initialize flash timer 303 and change the annunciator status to turn on alarm and turn off HOLD 305. The system then inquires as to whether reset is pressed 307 and, if the response to this inquiry is "YES," the system will go to executive 309 and repeat the executive loop 223 illustrated in FIG. 11. If the response to this inquiry is "NO," the system will proceed to inquire as to whether the flash timer has expired 311. If the response to this inquiry is "YES," the system will toggle the alarm light 313 and reset the timer 315. If the response to the flash timer expired inquiry 311 is "NO" or the timer is reset 315, the system will proceed to inquire as to whether there is weight on mat 317. If the response to this inquiry is "YES," the system will go to monitor 319 and repeat the monitor loop 273 illustrated in FIG. 13. If the response to the weight on mat inquiry 317 is "NO," the system will inquire as to whether the delay timer expired 321. In this step, the system determines whether the time selected by the caretaker to elapse after weight has left the mat and before weight has returned to the mat has expired. If the response to this delay time expired inquiry 321 is "NO," the system will return to the reset pressed inquiry 307 of the alarm loop 301. If the response to the delay timer expired inquiry 321 is "YES," the system proceeds to loop A 323 of the alarm mode illustrated in FIG. 15 to provide the audio alarm. In this phase of the alarm mode 301, the system will set the volume 325 and initialize the alarm variables 327 established by the caregiver for the system. The system then dispatches for selected tone 329, causing the monitor to give the audio tone selected from the six audio tones available to the caregiver. The system will also exercise relay per selected option 331, causing the nurse call station relay K1 to function according to one of the four alternatives selected by the caregiver for the system. The system will next inquire as to whether the reset is pressed 333. If the reset button 53 has not been operated by the caregiver, the response to the inquiry is "NO" and the system will return to the dispatch for selected tone 329 step of the alarm loop 301 and continue to provide the selected audio alarm. If the response to the reset press inquiry 333 is "YES," the system will bump event counter, save response time and total response 335 in which the system makes a record of the responses and response times of the caregiver. When this has been completed, the system will go to executive 337 and return to the executive loop 223 lustrated in FIG. 11.

Figure 16:
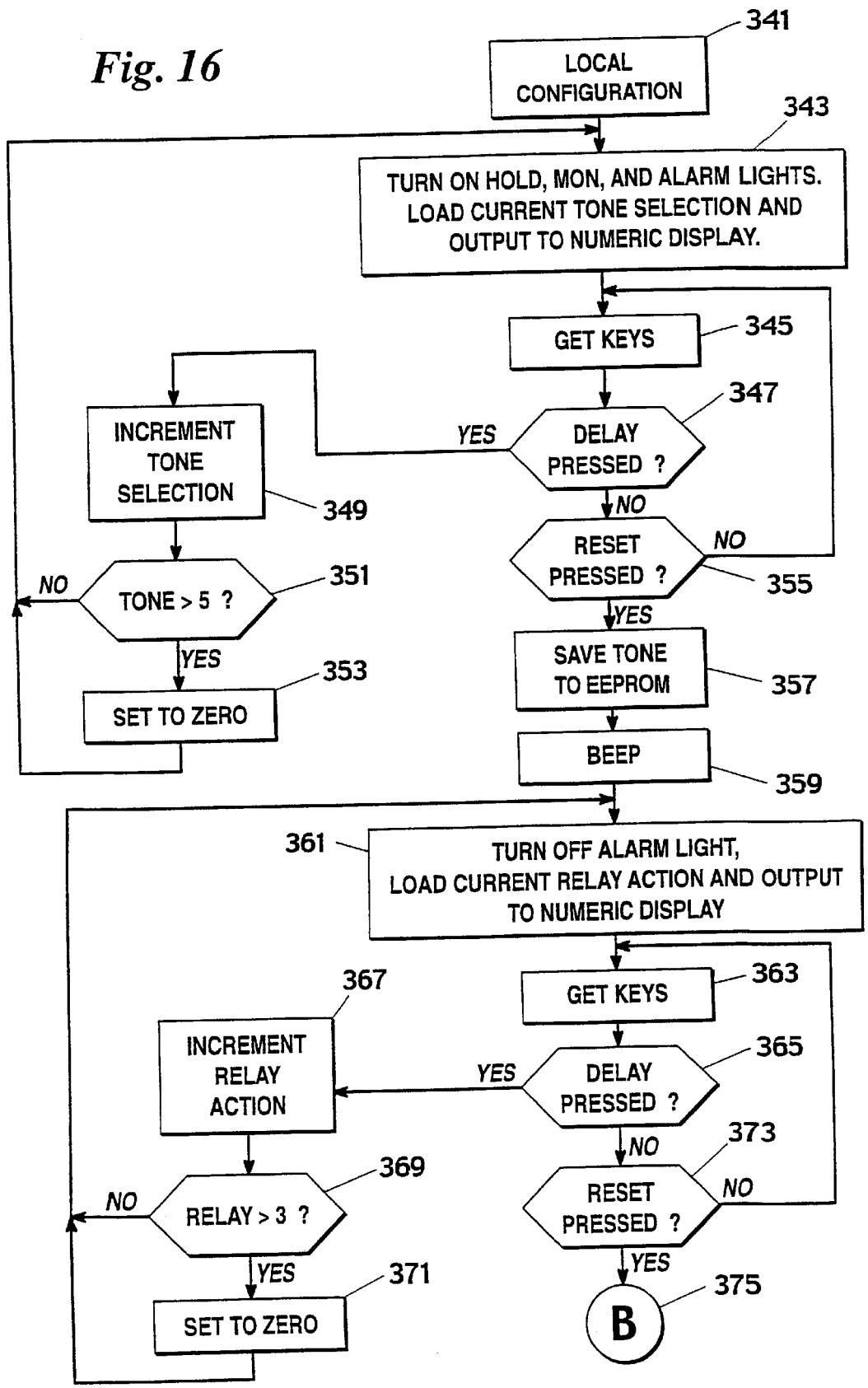
FIG. 16 is a flow diagram illustrating a portion of a preferred embodiment of the program mode of the monitor.

The local configuration or program mode 341 provides the user with a means to select various user options and save these selections in the non-volatile memory 131. As is best illustrated in FIG. 16, to enter this mode 341, the delay time is set to nine seconds. The monitor is then powered down. The monitor then is re-powered up with the reset button 53 pressed. The software will then illuminate multiple annunciators to indicate the particular phase of the programming mode 341 which has been entered. There are four phases of the program mode 341 including tone select, relay action & pull-out detection enable, hold time select and volume adjust. The tone select phase will display the last tone selected in the numeric display 41. A new tone may be chosen by cycling through the available options with the delay adjust button 55. Preferably, the default for the first time to apply power is the 1 kHz beep at 0.5 second intervals mentioned above. The relay action phase will display the current relay action in the numeric display 41. A different action may be chosen by cycling through the available options with the delay adjust button 55. The default for the first time to apply power is continuous operation. The available relay options are discussed above in relation to the alarm mode 301. Programming to a three will disable the pull-out detection. This allows the unit to be used in facilities which do not have a nurse call system or choose not to connect to the nurse call system. Programming this to a zero, one, or two enables the pull-out detection. The hold time phase allows the user to adjust the time delay between a patient placing weight on the mat and the beginning of monitoring. The default is preferably 10 seconds. The user may select 1 to 10 seconds. A zero in the numeric display 41 represents 10 seconds. The volume adjust allows the user to select one of ten possible volume levels. The alarm is silent when set to zero and at full volume when set to nine. The software translates 1 through 9 into actual steps (0–31) of the wiper control VW of the programmable volume control 71. When programmed from the external interface, all 32 steps are available. The default volume is seven (numeric displayed value) which translates to a wiper position of 25. For all of the above, a value is accepted and the next phase is entered by pressing the reset button 53. After the programming of the volume control 71, the monitor enters the hold mode 247. If power is removed during the programming process, the new values up to the last time reset 53 was pressed will be saved.

Figure 17:
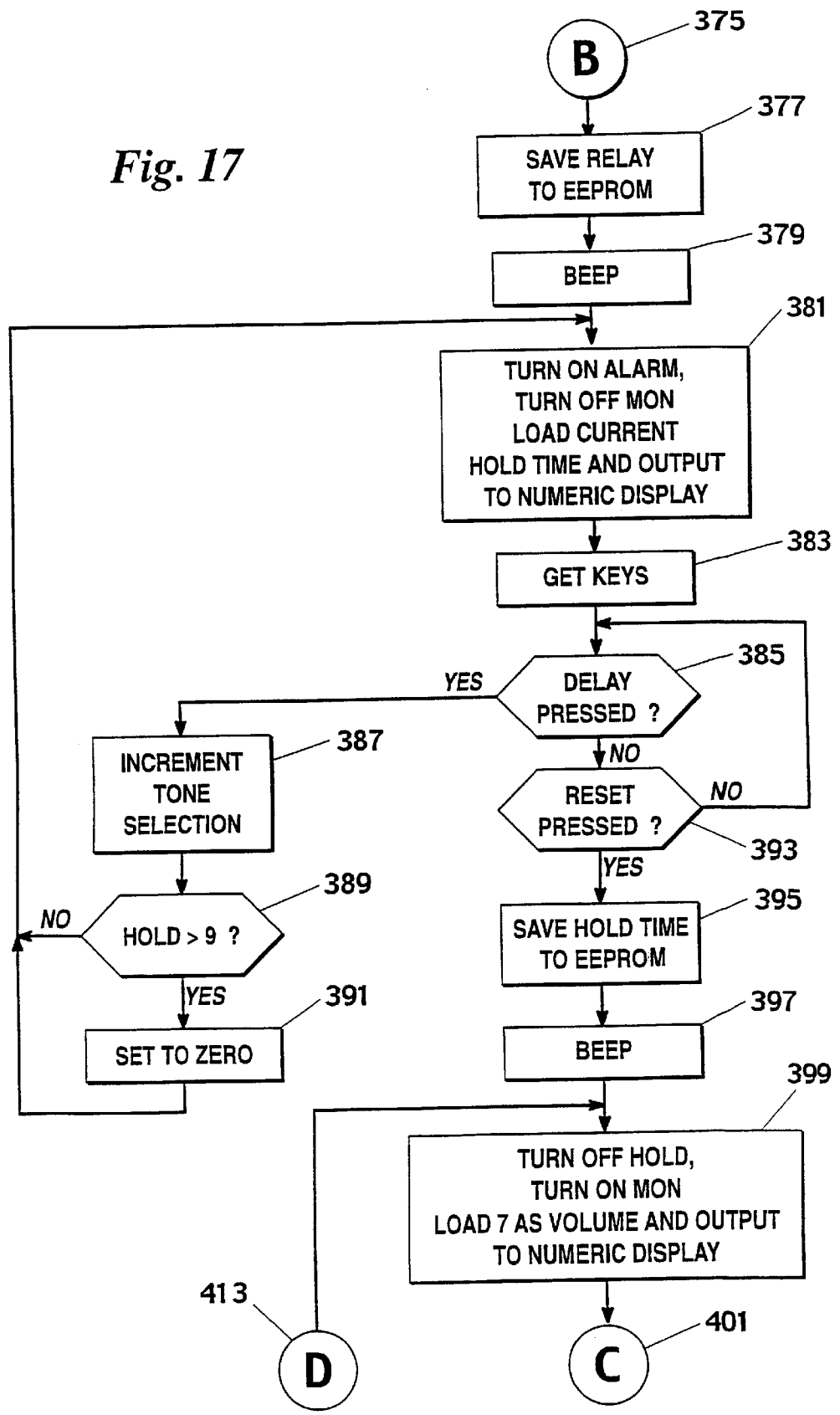
FIG. 17 is a flow diagram illustrating a portion of a preferred embodiment of the program mode of the monitor.
Figure 18:
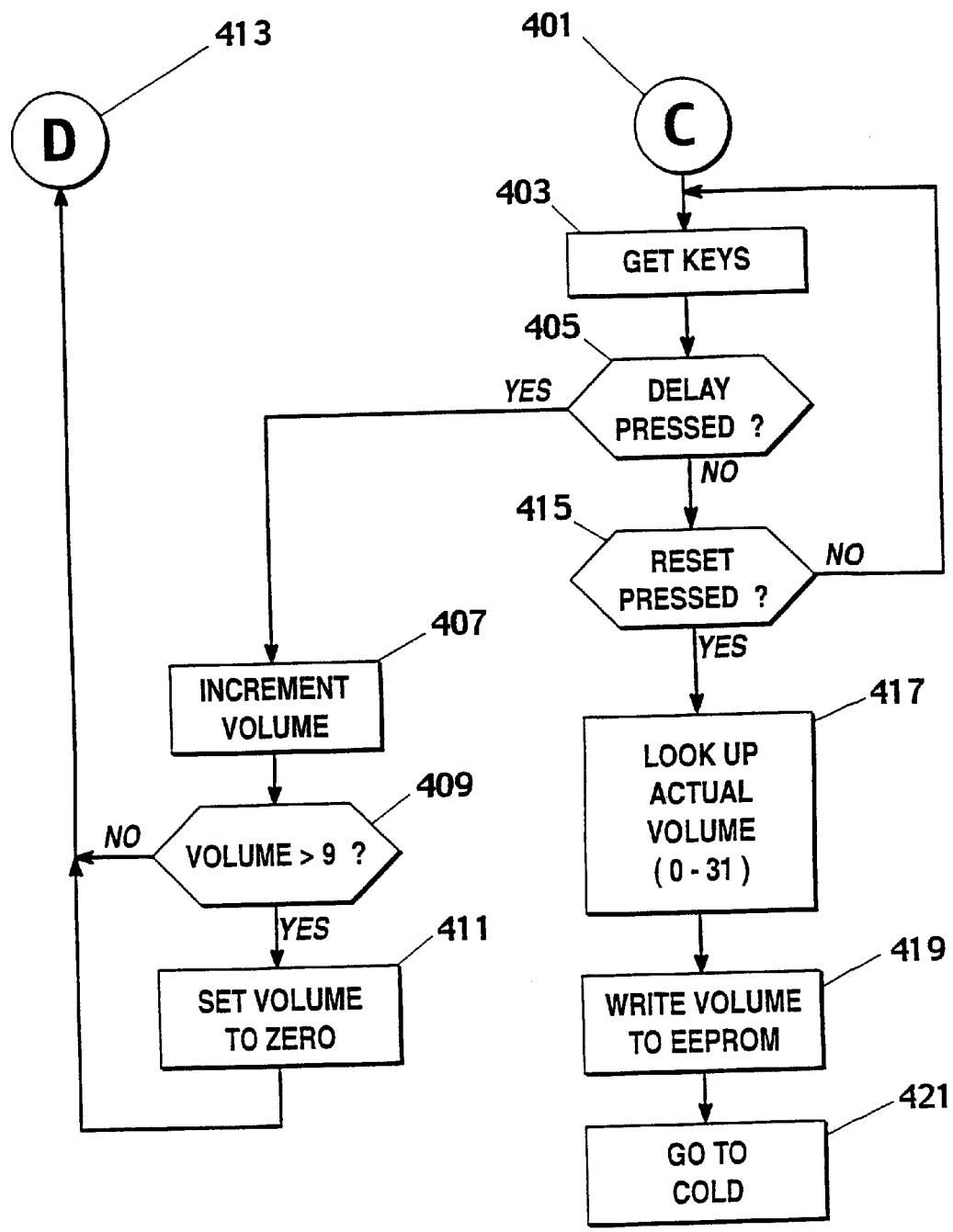
FIG. 18 is a flow diagram illustrating a portion of a preferred embodiment of the program mode of the monitor.

In the local configuration loop 341, the system will first turn on hold, monitor and alarm lights, load tone selection and output to numeric display 343. The system then proceeds to get keys 345 as earlier discussed with respect to other system loops, inquiring as to whether the delay adjust is pressed 347. If the response to this inquiry is "YES," the system will increment the toning selection 349 and then inquire as to whether the tone is greater than five 351. This relates to the sequence of six tones earlier referenced in relation to the alarm mode 301. If the response to this inquiry 351 is "YES," the system will reset the alarm mode to zero 353. If, after incrementing tone selection 349 the tone is not greater than five 351 or is set to zero 353, the system returns to the turn-on hold, monitor and alarm lights, load current tone selection and output numeric display step 343. If the response to the delay adjust pressed inquiry 347 is "NO," the system next inquires as to whether the reset is pressed 355. If the answer to this inquiry 349 is "NO," the system returns to the get keys step 345. If the response to this inquiry 349 is "YES," the system will save tone to EEPROM 357. When the tone has been saved in EEPROM 101, the system will beep 359 to indicate this status. The system will then turn off alarm light, load current relay action and output to numeric display 361 and again proceed to get keys 363. The system again inquires as to whether the delay adjust is pressed 365. If the response to this inquiry 365 is "YES," the system will increment relay action 367 according to the sequence discussed in relation to the alarm mode 301. The system will inquire as to whether the relay is greater than three 369, determining which increment of the relay options the system will select. If the response to this inquiry 369 is "YES," indicating that the option will be greater than three, the system sets to zero 371 to begin a recycle of available selections. If the answer to the inquiry 369 is "NO" or if the selection is set to zero 371, the system returns to the turn off alarm light, load current relay action and output to numeric display step 361. If the response to the delay adjust pressed inquiry 365 is "NO" the system proceeds to inquire as to whether the reset is pressed 373. If the answer to this inquiry is "NO," the system returns to the get keys step 363. If the answer to this inquiry is "YES," the system proceeds to point B375 of FIGS. 16 and 17. Looking at FIG. 17, if the reset pressed inquiry 373 response is "YES," the system will save relay to EEPROM 377, storing the selected relay position in the EEPROM 101. The system then proceeds to beep 379 to advise the caregiver of the status. The system then turns on the alarm annunciator, turns off the monitor annunciator, loads the current hold time and outputs to numeric display 381. The system then again proceeds to get keys 383, first inquiring as to whether the delay adjust is pressed 385. If the response to this inquiry is "YES," the system will increment hold time 387. Inquiry is made as to whether the hold is greater than nine 389 and if the response to this inquiry is "YES," the system will set to zero 391. If the response to the inquiry 389 is "NO," or the system has been set to zero 391, the system will return to the turn-on alarm enunciator, turn-off monitor enunciator, load current hold time and output numeric display 381. If the response to the delay adjust pressed inquiry 385 is "NO," the system will then inquire as to whether the reset is pressed 393. If the response to this inquiry is "NO," the system returns to the delay adjust pressed inquiry 385. If the response to the inquiry 393 is "YES," the system will save hold time to EEPROM 395, storing the selected delay time in the EEPROM 101. The system will then provide a beep 397 to indicate the status and will then turn off the HOLD annunciator, turn on monitor annunciator, load, e.g., 7 as the volume and output to the numeric display 399. That is, of the ten volume increments selectable, the system will automatically proceed to the seventh increment level. The system then proceeds through point C401 as illustrated in FIG. 18 to get keys 403 and inquire as to whether the delay adjust is pressed 405. If the response to this inquiry 405 is "YES," the system will increment volume 407 and inquire whether the volume is greater than nine 409. If the response to this inquiry 409 is "YES," the system will reset volume to zero 411. If the response to the volume greater than nine 409 is "NO," or the system has set the volume to zero 411, the system then returns through point D 413 to turn-off HOLD annunciator, turn-on monitor annunciator, load 7 as volume and output to numeric display 399 as shown in FIG. 17. Returning to FIG. 18, if the response to the delay adjust pressed inquiry 405 is "NO," the system proceeds to inquire as to whether the reset is pressed 415. If the response to this inquiry 415 is "NO," the system returns to the get key step 403. If the response to the inquiry 415 is "YES," the system proceeds to look up actual volume 417. The system then writes the volume to EEPROM 419, storing the selected volume in the EEPROM 101, and then goes to cold 421, returning to the cold start 201 illustrated in FIG. 10.

Figure 19:
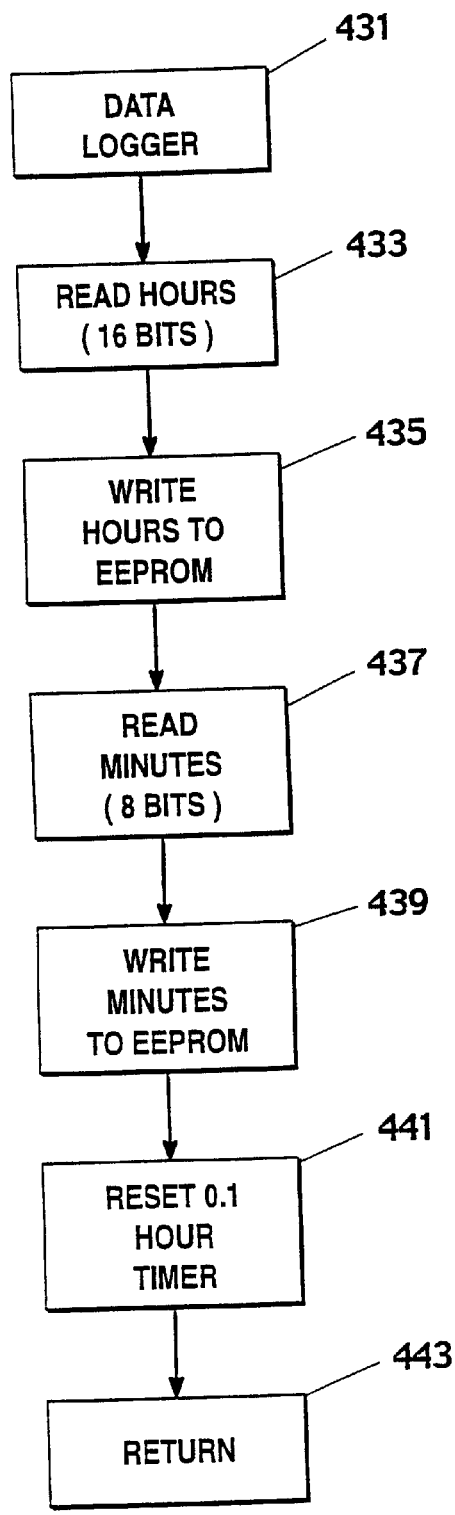
FIG. 19 is a flow diagram illustrating a preferred embodiment of the data logger subroutine of the monitor.

The data logger subroutine 431 illustrated in FIG. 19 is used by the system at the call data logger steps 239 and 279 of the executive loop 223 illustrated in FIG. 11 and the monitor mode 273 illustrated in FIG. 13, respectively. In the data logger sub routine 431, the system will read hours from RAM 433 and write hours to EEPROM 435, storing the number of hours that the system has operated in EEPROM 101. The system will then read minutes from RAM 437 and write minutes to EEPROM 439 to store any portion of an hour not already stored in EEPROM 101. The system will then reset 0.1 hour timer 441 and return 443 to the routine making the data logger demand.

Figure 20:
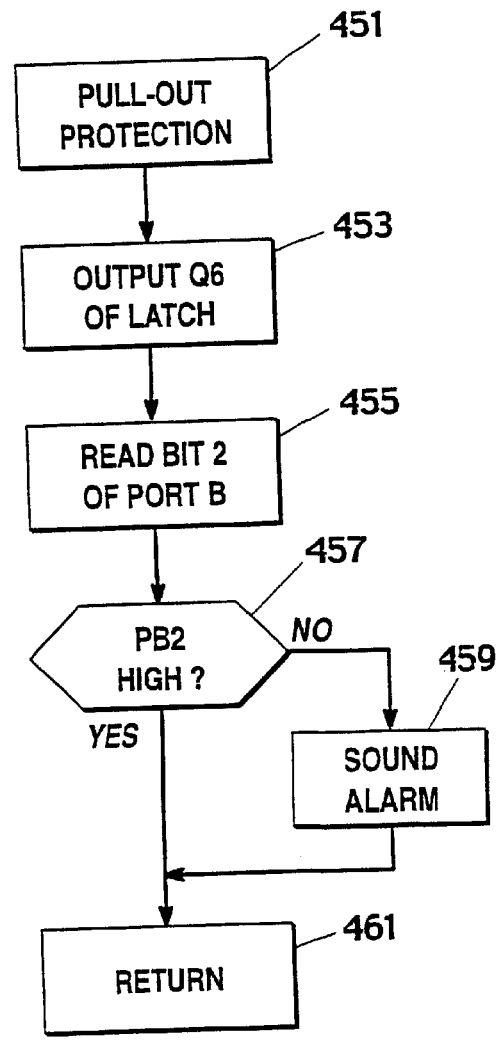
FIG. 20 is a flow diagram illustrating a preferred embodiment of the pull-out protection subroutine of the monitor.

The pull-out protection subroutine 451 illustrated in FIG. 20 is used by the system at the call pull-out steps 269 and 291 of the hold delay mode 247 illustrated in FIG. 12 and the monitor mode 273 illustrated in FIG. 13, respectively. In the pull-out protection subroutine 451, the system will read the output Q6 of the latch and read the status of Bit 2 of Port B 455. The system will then inquire as to whether PB2 is high 457. If the response to this inquiry is "NO," the system will sound alarm 459 and return 461 to the pull-out protection step 451. If the response to this inquiry is "YES," the system will proceed to return 461 to the routine making the pullout protection demand without sounding the alarm.

In summary, the monitor will preferably conform to the following

| Specification | Min: | Max: | Units | Tolerance |
|---|---|---|---|---|
| Delay Time | 1 | 10 | seconds | +/−5% |
| Hold Time | 1 | 10 | seconds | +/−5% |
| Relay One-shot Duration | 0.5 | 5 | seconds | n/a |
| Relay Asynchronous On | 0.25 | 2 | seconds | n/a |
| Relay Asynchronous Off | 0.25 | 2 | seconds | n/a |
| Tone Programming | 0 | 7 | n/a | n/a |
| Relay Programming | 0 | 2 | n/a | n/a |
| Pull-out Programming | 0 | 1 | n/a | n/a |
| Hold Time Programming | 0 | 9 | n/a | n/a |
| Warning Frequencies | n/a | n/a | Hertz | +/−10% |
| Tone Durations | n/a | n/a | seconds | +/−10% |

Microprocessor-Based Monitor with a Modifiable Personality

According to a second aspect of the instant invention, there is provided a microprocessor based monitor substantially as described above, but wherein the software that controls the actions of the monitor is stored within modifiable nonvolatile memory (e.g., flash-RAM) within the device, so as to be modifiable to create a patient monitor that has different personalities, depending on the needs of a particular application. More specifically, it is contemplated that much, if not all, of the software illustrated in FIGS. 10 to 20—the software that controls the personality/ functionality of the unit—will be stored within the monitor in a form that can be modified to suit the requirements of any site or individual patient (per doctor's orders) and, more particularly, the needs of the particular nurse call station to which the monitor is connected.

Figure 21:
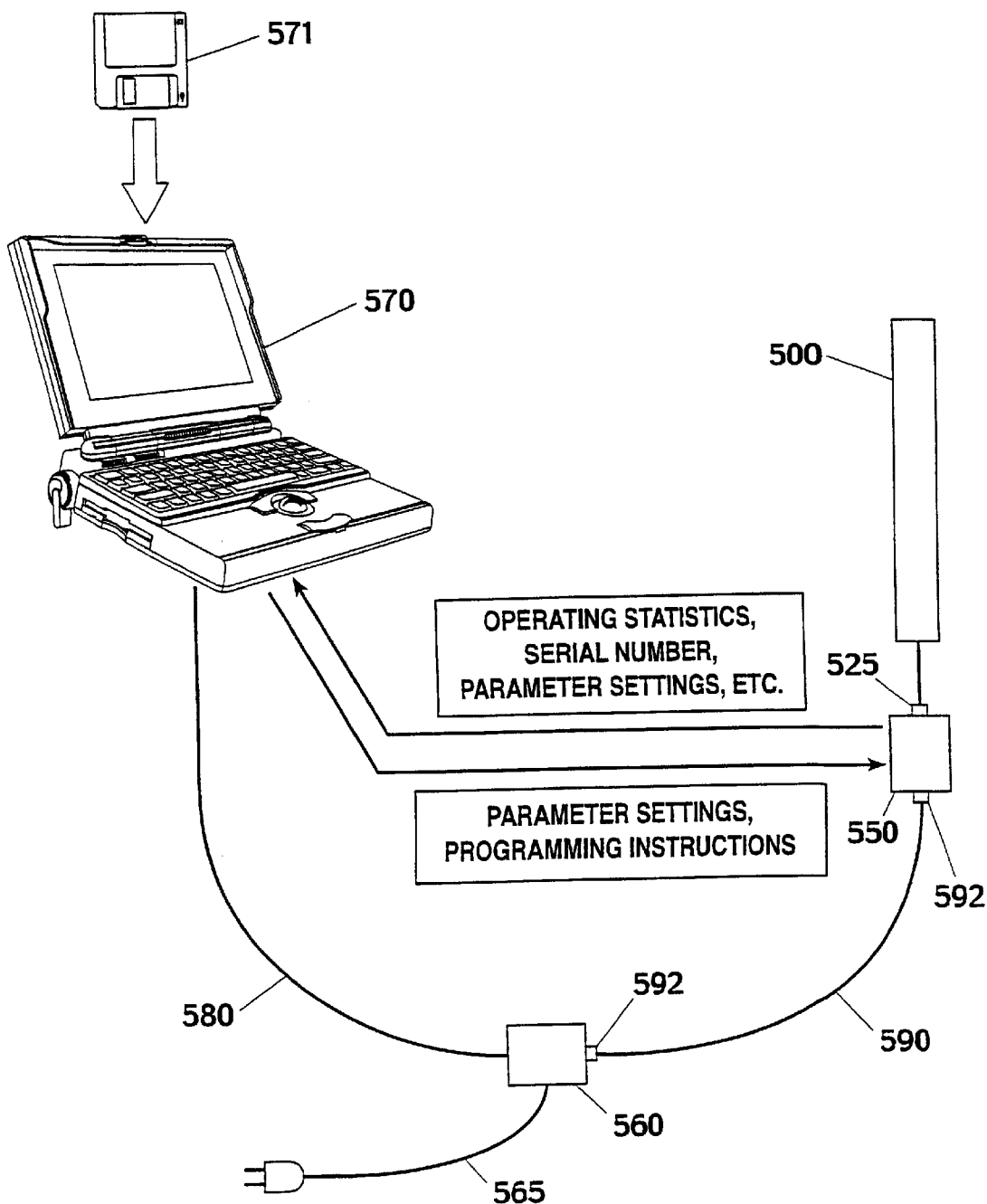
FIG. 21 contains an illustration of the general environment of the instant invention, wherein a host computer is connected to the monitor for purposes of data transfer.

Turning first to FIG. 21 wherein the general environment of the instant invention is broadly illustrated, in the preferred embodiment the reprogrammable monitor 550 is connected to sensing mat 500 by way of an RJ-11 connector 525. As has been discussed previously, the RJ-11 connector 525 provides the internal microprocessor 10 access to the state of the patient detector circuit within the mat 500. During normal operations, power line 565 would be plugged into monitor 550 to provide a source of external power to the unit. However, FIG. 21 illustrates the preferred configuration of the monitor 500 and a interconnected computer host 570 during exchange of information. Interface unit 560 is designed to act as a data conduit and pass serial information along line 580 from the host computer 570 to the monitor 550 and back again on demand from the host 570 or monitor 550. Additionally, the instant interconnection incorporates a power line into the serial line 590 for use by the monitor 550 during programming. It is not essential that the power be incorporated into the interconnecting line 590, but it is part of the presently preferred embodiment that it be so designed. In the event that a source of power is not needed via line 590, that line could take the form of a simple parallel serial, USB, etc. cable and interface unit 560 could then be a standard computer port (serial, parallel, etc.). Additionally, it should be noted that, although the interface unit 560 is pictured as being a separate device that is external to both the monitor 550 and the host 570, it might easily be incorporated into one unit, or the other, or both.

In the preferred embodiment, the lines 580 and 590 that interconnect the host computer 570 and electronic monitor 550 are serial lines, and the data communications protocol used is the I2C standard. However, those skilled in the art will recognize that there are many other standard and non-standard communications protocols that could be used in the alternative. For example, the instant inventors specifically contemplate that the interconnecting communications lines (580 and 590) could be parallel cables. Further, it might prove to be desirable in some cases to put a separate data port on the monitor 550 which might be, for example, a serial or parallel connector and which is dedicated for use in communications with a host computer 570, i.e., it does not share the responsibility of conveying power to the unit during data transfer. Additionally, it specifically contemplated by the inventors that it would even be possible to communicate with a remotely positioned monitor 550 through nurse call interface 130 (FIG. 1), thereby eliminating the need to physically bring together the host computer 570 and monitor 550, it being well within the capability of one of ordinary skill in the art to modify the invention-as-disclosed to implement this variation. Finally, although the preferred embodiment employs a hard-wired connection between the host computer 570 and the patient monitor, those of ordinary skill in the art that wireless connectivity is a natural way to make this interconnection, including wireless connectivity via IR or other communications means.

Figure 22:
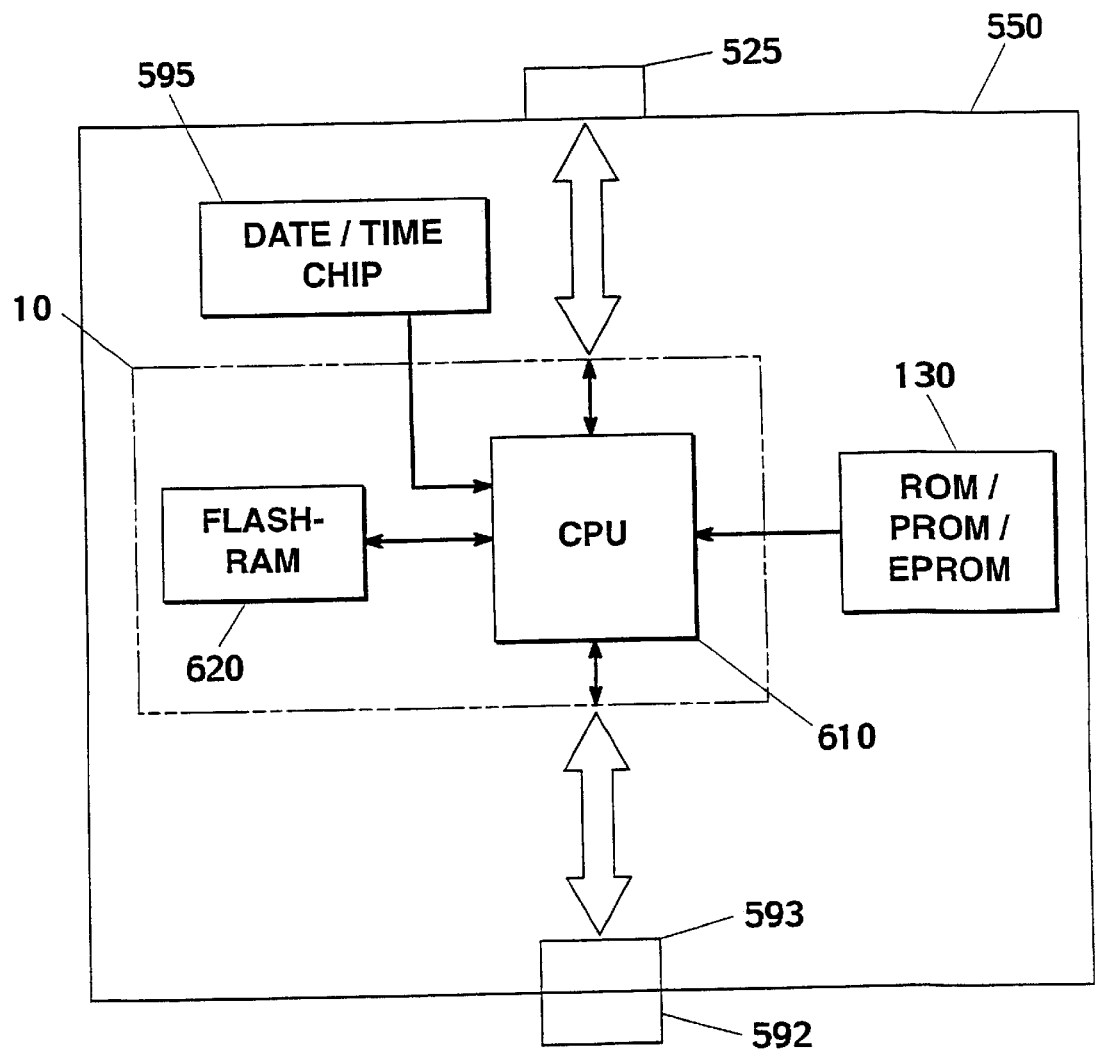
FIG. 22 illustrates the main hardware elements of the reprogrammable monitor embodiment.

Within the monitor 550 and as is illustrated in FIG. 22, data sent from the host computer 570 are received by the CPU 620 of the microprocessor 10 and then subsequently stored, preferably within a local flash RAM 610. As is well known to those skilled in the art, many other similar arrangements might be used instead that would be functionally equivalent to using flash RAM, including using conventional RAM with battery backup, EEPROM, a local disk drive, etc, the key feature being that—what ever type of storage is used—it should be at least relatively nonvolatile for purposes of the instant embodiment and, most importantly, modifiable under local program control. Thus, in the text that follows the phase "modifiable nonvolatile RAM" will be used in the broadest sense to refer to the type of storage just described. Additionally, it is anticipated that CPU 620 will be provided with some amount of ROM 130 or other storage type for permanently storing information and which could contain, for example, the serial number of the unit, date of manufacture, and the code that would control the basic operations of the CPU 10 during cold starts, resets, personality uploads, etc.

During operation, the monitor 550 could use the flash RAM 620 as storage for various data parameter values including accumulated performance statistics, data/time stamps of alarm events, patient identification numbers, hold delay, delay time, speaker volume, type of alarm tone (i.e., what sort of alarm will be sounded—e.g., fast beep, slow beep, whoop, etc.), relay action type (e.g., continuous, one-shot, asynchronous, etc.), total time in service, date of last bio-med check, total number of alarms sounded, response time to last alarm, average response to last four alarms, alarm history (e.g., response times for the last fifteen or so alarms and time/date of alarm occurrence), repair history, hospital equipment identification number (e.g., asset number), or a current time/date stamp. Additionally, this same connection could be used to read parameters from the monitor 550 such as total time in service, date of last biomedical check, the unit serial number, etc.

However, the main anticipated use for the flash RAM 620 is for storage of the operating personality of the unit. In particular, FIGS. 10 to 20 discussed previously are implemented within the monitor in the form of assembly language computer instructions which are stored in and read from ROM memory 130, thereby making those program steps immutable, unless the memory chip containing them is replaced. In the instant embodiment, it is anticipated that much of the functionality of the software illustrated in those figures would be stored in a form that can be modified to suit the requirements of a particular nurse call station, or hospital environment, e.g., within flash RAM 620.

Figure 23:
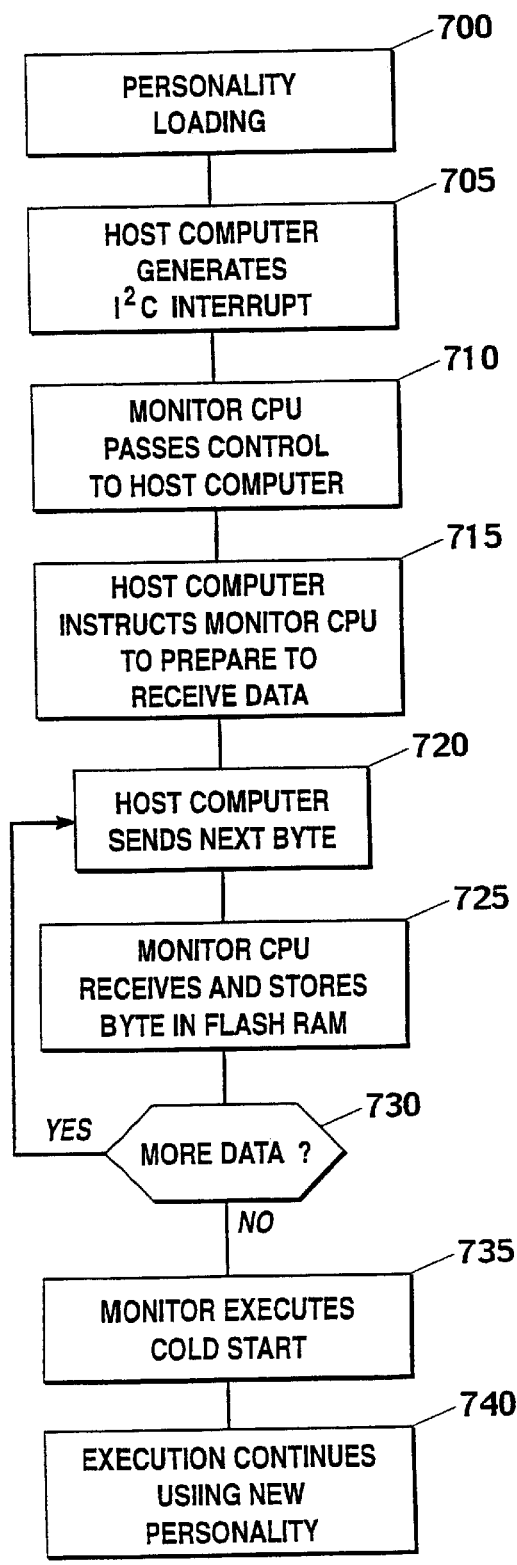
FIG. 23 contains a flow chart that illustrates the principle computer steps in the personality loading routine.

As is broadly illustrated in FIG. 23, the personality loading program 700 within the monitor 550 is preferably initiated through the use of a non-maskable interrupt 705 (defined as a "master mode" interrupt) as is provided for by the I2C communications standards. In more particular, when the CPU 610 senses an interrupt on the pins associated with port 593, it preferably enters a slave mode, wherein the host computer 570 completely controls its operations. The host computer 570 then directs the monitor CPU 610 to begin receiving "data" 715 and storing that data 725 at predetermined locations within the flash RAM 620, which data may be parameter values as discussed previously or, preferably, binary computer instructions that define the personality/operations of the unit.

At the conclusion of the loading process, the host computer will preferably require the monitor to execute a cold start 735, after which the monitor will continue execution as before, only this time using the various aspects of the new personality stored 740 in flash-RAM. Of course, the obvious advantage of an arrangement such as this is that it permits the functionality of the monitor to be modified to suit specific applications and, indeed, makes it possible for a single monitor to function with multiple nurse call station formats with only minimal effort.

System for Programming a Reprogrammable Monitor

According to still a further aspect of the instant invention, there is provided a monitor/host software combination that allows the end-user to make personality changes in the software that controls the monitor. Additionally, this same system provides a means for the user to read and/or modify data values that are maintained in the nonvolatile memory of the patient monitor. In the preferred embodiment, the software that manages the user interface would run on a host computer 570 such as a lap top computer. As is well known to those skilled in the art, the software embodying the instant invention might be conveyed into the computer that is to execute it by way of any number of devices 571 including, for example, a floppy disk, a magnetic disk, a magnetic tape, a magneto-optical disk, an optical disk, a CD-ROM, flash RAM, a ROM card, a DVD disk, or loaded over a network.

As is broadly illustrated in FIGS. 21 through 23 and as has been discussed previously, a preferred embodiment of the instant invention uses a host computer 570 to load operating parameters and executable instructions into the monitor. Additionally, this same connection is used to retrieve statistical and other information from the monitor. Further, cumulative statistical values such as total time spent in an alarm condition, alarm history, etc., can be reset (e.g., made equal to zero) by this same process.

Figure 24:
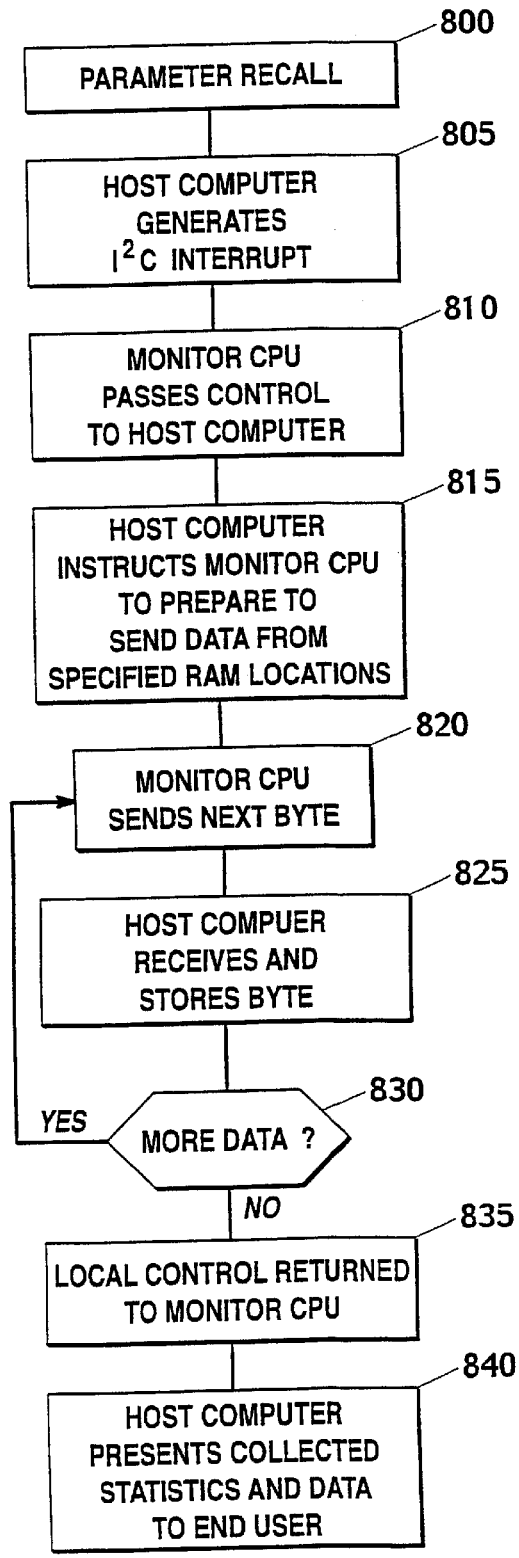
FIG. 24 is a flow chart of the principle steps in the parameter recall routine, wherein data is passed from the monitor to the host CPU.

As is illustrated in FIG. 24, the host control program for parameter and operating statistics recall 800 preferably begins by generating a non-maskable interrupt 805 which results in monitor 550 passing operating control to the host computer 570. The host computer 570 then instructs the monitor CPU 610 to pass the contents of specific memory locations (steps 815 to 830) back to itself. The data returned from the monitor 550 are then presented to the user for review. Needless to say, once the data have been collected additional analysis of the resulting information would certainly be useful in some situations and that additional step has been specifically contemplated by the instant inventors.

Additional Embodiments

Those of ordinary skill in the art will recognize that there are many active devices that could serve for purposes of the instant invention as the microprocessor 10 including, of course, a conventional microprocessor. More particularly, the instant invention minimally requires that the microprocessor 10 be an active device, i.e., one that is programmable in some sense, is capable of recognizing signals from a bed mat or similar patient sensing device, and is capable of digitally synthesizing alarm sounds (e.g., either via a mathematical algorithm or playback of a digital recording) for use by speaker 75. Of course, these sorts of modest requirements may be satisfied by any number of programmable logic devices ("PLD") including, without limitation, gate arrays, FPGA's (i.e., field programmable gate arrays), CPLD's (i.e., complex PLD's), EPLD's (i.e. erasable PLD's), SPLD's (i.e. simple PLD's), PAL's (programmable array logic), FPLA's (i.e., field programmable logic array), FPLS (i.e., fuse programmable logic sequencers), GAL (i.e., generic array logic), PLA (i.e. programmable logic array), FPAA (i.e. field programmable analog array), PsoC (i.e. programmable system-on-chip), SoC (i.e. system-on-chip), CsoC (i.e., configurable system-on-chip), ASIC (i.e. application specific integrated chip), etc., as those acronyms and their associated devices are known and used in the art. Further, those of ordinary skill in the art will recognize that many of these sorts of devices contain microprocessors integral thereto. Thus, for purposes of the instant disclosure the terms "processor," "microprocessor" and "CPU" (i.e. central Processing unit) should be interpreted to take the broadest possible meaning herein, and such meaning is intended to include any PLD or other programmable device of the general sort described above.

Figure 25:
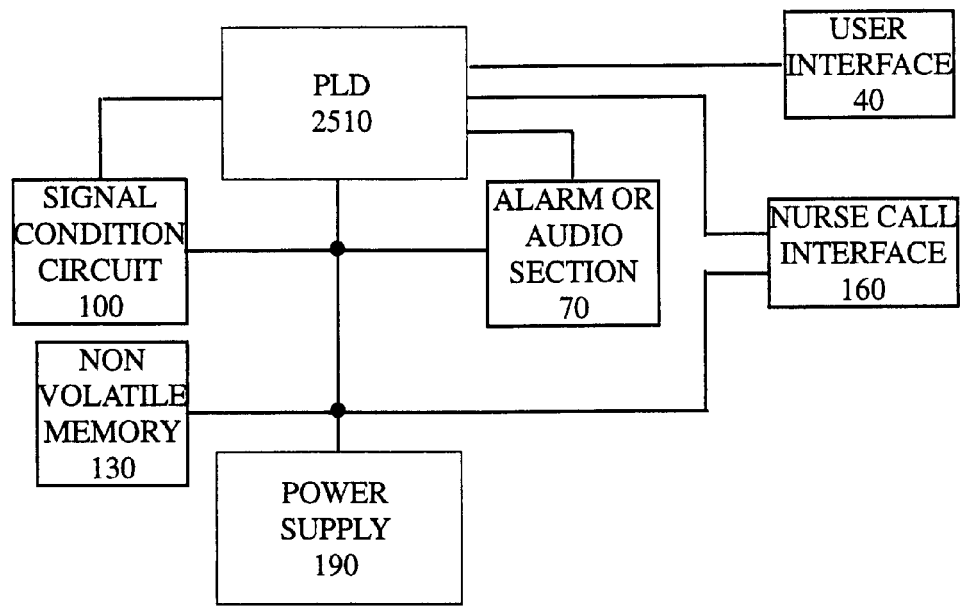
FIG. 25 contains a schematic illustration of another preferred embodiment of the instant invention wherein a gate array is substituted for microprocessor.
Figure 27:
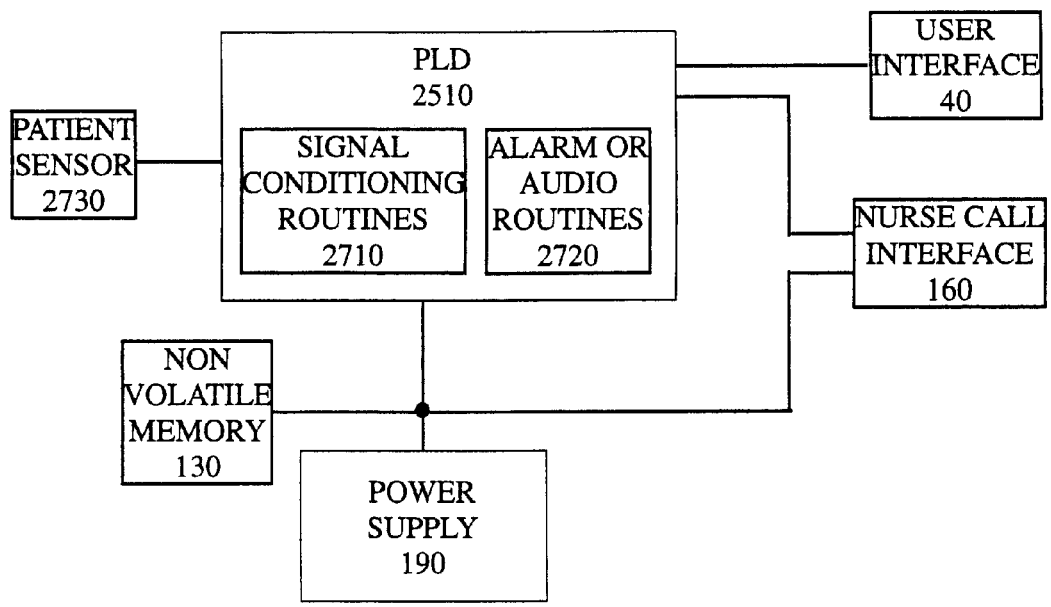
FIG. 27 contains a schematic illustration of another preferred embodiment, wherein the signal conditioning function and audio/alarm functions are implemented in software rather than hardware.

Turning now to FIG. 25, as can be seen by comparison with FIG. 1 PLD 2510 has simply been substituted in place of microprocessor 10 in that figure and functions both to sense the presence or absence of the patient and to synthesize the alarm sound according to its programming. Additionally, and in still another preferred arrangement FIG. 27 illustrates a variation wherein the signal conditioning circuit 100 has been implemented within the PLD 2510 in the form of software routines 2710 (e.g., the debounce circuitry which would preferably be a part of hardware circuit 100 would be implemented as software for execution by the PLD 2510 according to methods well known to those of ordinary skill in the art). Additionally, the audio or alarm section 70 has similarly been implemented as software and/or hardware within the PLD 2720 (i.e., the power amplifier 73 and volume control 71 have been implemented within the microprocessor in the form of software and/or hardware). As has been discussed elsewhere, patient sensor 2730 is positionable to be in electronic communication with the PLD 2510 and, in a preferred arrangement, will be a pressure sensitive mat, wetness sensor, or other device for monitoring a patient's condition.

Figure 26:
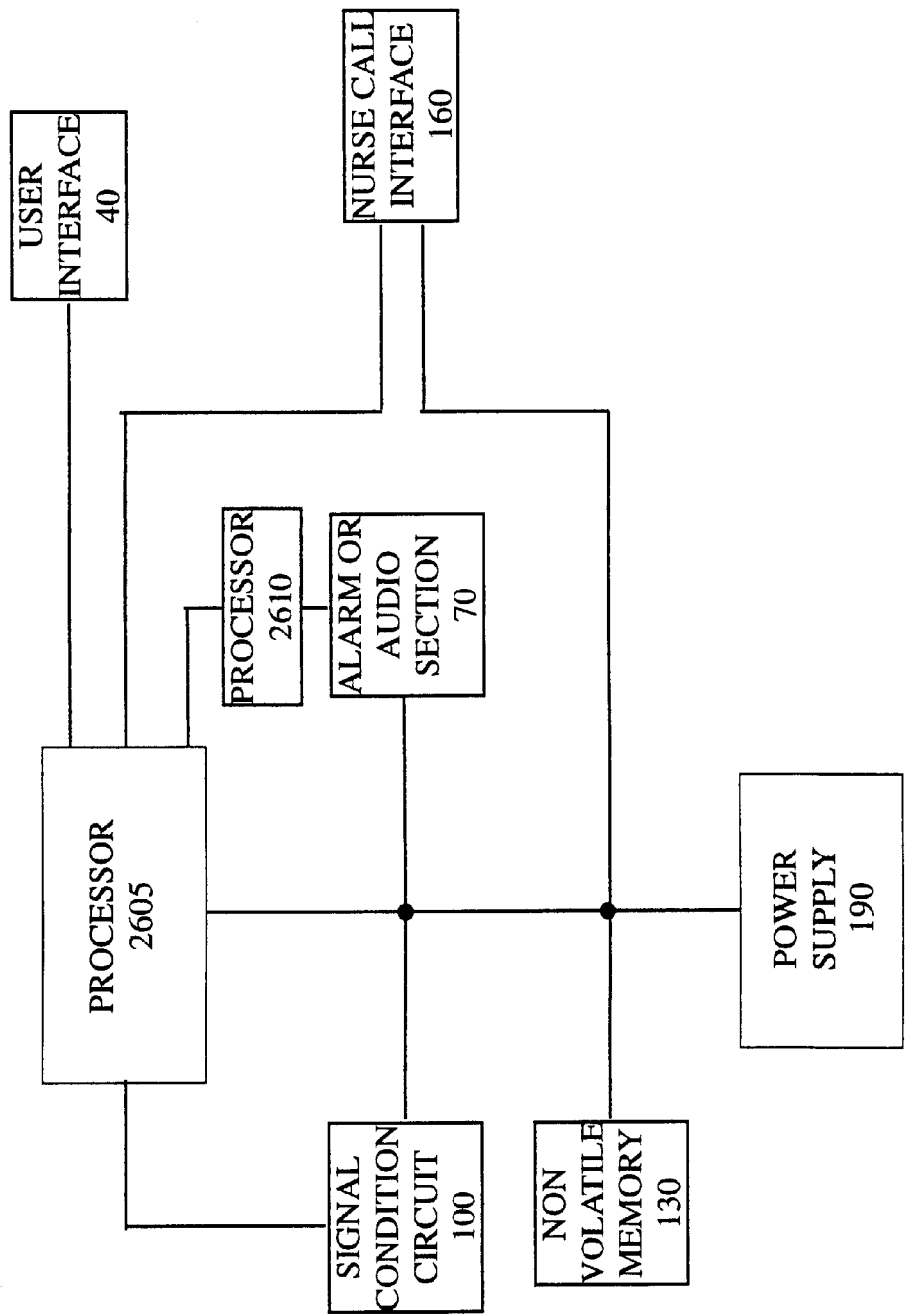
FIG. 26 illustrates a preferred embodiment, wherein two microprocessors are utilized to control the instant patient monitor and alarm.

It should be noted that it is not essential to the operation of the instant invention that the tasks of patient monitoring and alarm synthesis both be handled by a single PLD or microprocessor 10. For example and as is illustrated in FIG. 26, it should be clear to those of ordinary skill in the art that two interconnected PLDs/microprocessors could readily be used: one to monitor the position of the patient and another to synthesize the alarms when directed to do so by the first processor. Thus, the two PLDs in essence divide up the responsibilities of the single-microprocessor embodiment (e.g., FIG. 1) microprocessor and each performs a subset of its tasks.

More generally, multiple interconnected CPU's could be used, each performing a specific function related to patient monitoring. In FIG. 26, note that a preferred embodiment of the instant invention utilizes a first PLD/processor 2605 which is programmed to direct a second PLD/processor 2610 to synthesize the alarm sounds, the second processor 2610 being the device that actually drives the audio section 70. Thus, for purposes of the instant disclosure the terms "processor" and "microprocessor" should be interpreted in their broadest sense to include a PLD or single dedicated microprocessor that controls all of the functions of the instant invention (e.g., patient monitoring, alarm synthesis, etc., as illustrated in FIG. 1), as well as multiple/interconnected and coordinated microprocessors/PLDs, each of which controls some specific aspect of the functioning of the patient monitor.

Conclusions

Although the preceding text has occasionally referred to the electronic monitor of the instant invention as a "bed" monitor, that was for purposes of specificity only and not out of any intention to limit the instant invention to that one application. In fact, the potential range of uses of this invention is much broader than bed-monitoring alone and might include, for example, use with a chair monitor, a toilet monitor, or other patient monitor, each of which is configurable as a binary switch, a binary switch being one that is capable of sensing at least two conditions and responding to same via distinct electronic signals. In the preferred embodiment, those two conditions would be the presence of patient and the absence of a patient from a monitored area. Although a pressure sensitive switch is the binary switch of choice for use in the preferred embodiment, other types of switches could work as well for some applications. Additionally, it should be noted that the use of the term "binary" is not intended to limit the instant invention to use only with sensors that can send only two signal types. Instead, binary switch will be used herein in its broadest sense to refer to any sort sensor that can be utilized to discern whether a patient is present or not, even if that sensor can generate a multitude of different of signals.

Finally, it should be noted and remembered that the term "digital synthesis" as used in the context of generating alarm sounds, should be interpreted in its broadest sense to include any sort of sound that is generated by the PLD under software control. That could include something as complex as playing a "MIDI" file or an MP3 or other digital sound file (e.g., a .WAV file, a .SND file, etc.) through the loudspeaker or as simple as repeatedly turning the speaker "on" and "off" under microprocessor control to create a sound.

Thus, it is apparent that there has been provided, in accordance with the invention, a monitor and method of operation of the monitor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. A bed patient monitor comprising:
   (a) a loudspeaker, said speaker for producing at least one alarm sound therefrom; and,
   (b) a processor in electronic communication with said loudspeaker, said processor
      (1) for receiving electronic signals from a sensor indicative of the presence thereon and absence therefrom of a patient,
      (2) for activating said patient monitor to an alarm mode in response to said electronic signals,
      (3) for synthesizing at least one alarm sound under software control, and,
      (4) for transmitting to said loudspeaker said synthesized alarm sound.

2. A bed patient monitor according to claim 1, wherein said processor comprises:
   (b1) a first CPU in electronic communication with said loud speaker, said first CPU
      (i) for synthesizing at least one alarm sound under software control,
      (ii) for transmitting said synthesized alarm sound to said loudspeaker, and
   (b2) a second CPU in electronic communication with said first CPU, said second CPU
      (i) for receiving electronic signals from said sensor indicative of the presence thereon and absence therefrom of the patient,
      (ii) for activating said patient monitor to an alarm mode in response to said electronic signals from said sensor,
      (iii) for sending a signal representative of the patient's presence or absence to said first CPU.

3. A monitor according to claim 1, wherein said processor is selected from a group consisting of a PLD, a gate array, a FPGA, a CPLD, a EPLD, a SPLD, a PAL, a FPLA, a FPLS, a GAL, a PLA, a FPAA, a PSoC, a SoC, an ASIC, and a CSoC.

4. A monitor according to claim 1, further comprising:
   (c) a programmable volume control in electronic communication with said processor, said programmable volume control being operable by said processor to select a decibel level of said at least one alarm sound, and,
   (d) a power amplifier in electronic communication with said programmable volume control and said loud speaker, said power amplifier
      for driving said loudspeaker, said power amplifier responding to an input signal derived from said programmable volume control to produce said at least one alarm sounds.

5. A monitor according to claim 4, wherein said processor is at least for operating said programmable volume control to select a decibel level of said at least one alarm sound.

6. A monitor according to claim 4 further comprising
   (e) a nurse call interface having a relay which is energized when said power amplifier is deenergized and having a normally open contact, a normally closed contact and a common contact for interconnecting the monitor to a nurse call system through one of said normally open and normally closed contacts.

7. A monitor according to claim 1 further comprising
   (c) memory accessible by said processor, said memory at least containing data representative of at least one alarm sound for selection by said processor.

8. A monitor according to claim 7, wherein the step of synthesizing at least one alarm sound under software control, comprises:
   (i) selecting a particular alarm sound from among said at least one alarm sounds, wherein said particular alarm sound having data representative thereof stored in said memory;
   (ii) accessing said data representative of said particular alarm sound, and,
   (iii) forming at least one synthesized alarm sound from said data representative of said particular alarm sound.

9. A monitor according to claim 8, wherein at least a portion of said memory is located internal to said processor.

10. A monitor according to claim 1 further comprising:
    (c) non-volatile memory for logging usage data associated with the operation of said bed patient monitor.

11. A monitor according to claim 10, wherein said usage data is selected from a group consisting of total hours of use of said monitor, total time of alarm sounding by said monitor, total number of alarms sounded by said monitor, patient data, a response time, and combinations thereof.

12. A monitor according to claim 11 having a communications port for downloading said logged usage data to a host computer.

13. A bed patient monitor according to claim 1, wherein the step of synthesizing at least one alarm sound under software control comprises the step of algorithmically synthesizing at least one alarm sound under software control.

14. A patient monitor, comprising:
    (a) a patient sensor, said patient sensor positionable to be proximate to a patient,
       (1) said patient sensor for detecting at least one state of the patient,
       (2) said patient sensor being responsive to a change in the detected at least one state of the patient, and,
       (3) said patient sensor responding electrically to said change in the detected at least one state of the patient;
    (b) a loudspeaker, said speaker for producing audible alarms; and,
    (c) a processor in electronic communication with said loudspeaker and said patient sensor, said processor containing therein at least a portion of a computer program, said computer program containing instructions at least for:
(1) selecting an alarm sound in response to said electrical change in said patient sensor,
(2) accessing at least one data item representative of said selected alarm sound,
(3) synthesizing an alarm sound from said at least one data item representative of said selected alarm sound, and,
(4) transmitting said synthesized alarm sound to said loud speaker to create an audible alarm.

15. A patient monitor according to claim 14, wherein said at least one data item representative of said selected alarm sound is stored in non-volatile memory.

16. A patient monitor according to claim 14, wherein said at least one data item representative of said selected alarm sound is stored in modifiable non-volatile memory.

17. A reprogrammable patient monitor for use with a binary switch, said binary switch at least for detecting a presence or an absence of a patient, comprising:
(a) a processor for synthesizing at least one sound under software control, said processor
  (a1) being positionable so as to be in electronic communication with said binary switch, and,
  (a2) responding to said binary switch when placed into electronic communication therewith,
(b) modifiable nonvolatile RAM accessible by said processor,
  (b1) said modifiable nonvolatile RAM containing at least a plurality of modifiable computer instructions utilizable by said processor, and,
  (b2) said modifiable computer instructions defining at least a portion of said response of said processor to said binary switch; and,
(c) a loudspeaker in electronic communication with said processor and responsive thereto, said loudspeaker for sounding for sounding said at least one synthesized sound.

18. A reprogrammable patient monitor according to claim 17, further comprising:
(d) a port for downloading information from and uploading information to a host computer, said microprocessor being in electronic communication with said port.

19. A reprogrammable patient monitor according to claim 17, wherein said modifiable nonvolatile RAM further contains at least one data item.

20. A reprogrammable patient monitor according to claim 19, wherein said at least one data item is selected from the group consisting of a patient identification number, an alarm tone option, a relay action option, a hold delay, a delay time, a speaker volume, a total time in service, a date of last bio-med check, a total number of alarms sounded, a response time to a last alarm, an average response to a last four alarms, an alarm history, a repair history, and an hospital inventory number.

21. A reprogrammable patient monitor according to claim 17, wherein said binary switch is selected from the group consisting of a bed mat, a chair mat, an enuresis sensor, a toilet seat sensor.

22. An apparatus for altering a personality of a reprogrammable patient monitor, wherein is provided the reprogrammable patient monitor of claim 17, further comprising:
(d) a host computer, said host computer containing a plurality of data values for use by said reprogrammable patient monitor; and,
(e) an interface unit, said interface unit
  (e1) being in electronic communication with said host computer and with said reprogrammable patient monitor, and
  (e2) passing at least one of said plurality of data values between said host computer and said reprogrammable patient monitor upon demand.

23. A reprogrammable patient monitor according to claim 17, wherein
said loudspeaker is driven by a power amplifier,
said amplifier responding to an input signal derived from a programmable volume control to produce an aural alarm, and,
wherein said microprocessor operates said programmable volume control to produce a synthesized alarm under software control.

24. A bed patient monitor comprising:
(a) a loudspeaker, said speaker for producing at least one alarm sound therefrom; and,
(b) a processor in electronic communication with said loudspeaker, said processor
  (1) for receiving electronic signals from a sensor indicative of the presence thereon and absence therefrom of a patient,
  (2) for activating said patient monitor to an alarm mode in response to said electronic signals,
  (3) for internally synthesizing at least one alarm sound under software control, and,
  (4) for transmitting to said loudspeaker said synthesized alarm sound.

25. A bed patient monitor according to claim 24, wherein said processor comprises:
(b1) a first CPU in electronic communication with said loud speaker, said first CPU
  (i) for internally synthesizing at least one alarm sound under software control,
  (ii) for transmitting said synthesized alarm sound to said loudspeaker, and
(b2) a second CPU in electronic communication with said first CPU, said second CPU
  (ii) for receiving electronic signals from said sensor indicative of the presence thereon and absence therefrom of the patient,
  (ii) for activating said patient monitor to an alarm mode in response to said electronic signals from said sensor,
  (iii) for sending a signal representative of the patient's presence or absence to said first CPU.

26. A monitor according to claim 24, wherein said processor is selected from a group consisting of a PLD, a gate array, a FPGA, a CPLD, a EPLD, a SPLD, a PAL, a FPLA, a FPLS, a GAL, a PLA, a FPAA, a PSoC, a SoC, an ASIC, and a CSoC.

* * * * *